(12) United States Patent
Ruat et al.

(10) Patent No.: US 8,957,091 B2
(45) Date of Patent: Feb. 17, 2015

(54) USE OF QUINOLINONE DERIVATIVES AS A RESEARCH TOOL

(75) Inventors: Martial Ruat, Orsay (FR); Helene Faure, Gif-sur-Yvette (FR); Tatiana Gorojankina, Gif sur Yvette (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 13/885,098

(22) PCT Filed: Nov. 15, 2011

(86) PCT No.: PCT/IB2011/055098
§ 371 (c)(1),
(2), (4) Date: May 13, 2013

(87) PCT Pub. No.: WO2012/066479
PCT Pub. Date: May 24, 2012

(65) Prior Publication Data
US 2013/0236912 A1    Sep. 12, 2013

(30) Foreign Application Priority Data
Nov. 16, 2010 (FR) ..................... 10 04444

(51) Int. Cl.
| A61K 31/04 | (2006.01) |
| G01N 33/68 | (2006.01) |
| G01N 33/566 | (2006.01) |
| G01N 33/50 | (2006.01) |
| G01N 33/574 | (2006.01) |

(52) U.S. Cl.
CPC .............. *G01N 33/68* (2013.01); *G01N 33/566* (2013.01); *G01N 33/5008* (2013.01); *G01N 33/574* (2013.01); *G01N 2333/726* (2013.01); *G01N 2500/04* (2013.01)
USPC .......................................... 514/312; 546/159

(58) Field of Classification Search
USPC .......................................... 514/312; 546/159
See application file for complete search history.

(56) References Cited

U.S. PATENT DOCUMENTS

| 4,547,511 A | 10/1985 | Eriksoo et al. |
| 6,291,516 B1 | 9/2001 | Dudek et al. |
| 6,432,970 B2 | 8/2002 | Beachy et al. |
| 2005/0282231 A1 | 12/2005 | Tabin et al. |
| 2007/0218775 A1 | 9/2007 | Coronado |
| 2013/0267559 A1* | 10/2013 | Ruat et al. ................ 514/312 |

FOREIGN PATENT DOCUMENTS

| FR | 03/00646 | 9/2003 |
| WO | WO-99/52534 A1 | 10/1999 |
| WO | WO-00/41545 A2 | 7/2000 |
| WO | WO-01/19800 A2 | 3/2001 |
| WO | WO-01/26644 A2 | 4/2001 |
| WO | WO-01/27135 A2 | 4/2001 |
| WO | WO-01/74344 A2 | 10/2001 |
| WO | WO-02/30421 A2 | 4/2002 |
| WO | WO-02/30462 A2 | 4/2002 |
| WO | WO-2005/033288 A2 | 4/2005 |
| WO | WO-2005/042700 A2 | 5/2005 |
| WO | WO-2006/028958 A2 | 3/2006 |
| WO | WO-2006/080894 A2 | 8/2006 |
| WO | WO-2007/054623 A2 | 5/2007 |
| WO | WO-2007/059157 A1 | 5/2007 |
| WO | WO-2007/120827 A2 | 10/2007 |
| WO | WO-2008/014291 A2 | 1/2008 |
| WO | WO-2008/014307 A2 | 1/2008 |
| WO | WO-2008/075196 A1 | 6/2008 |
| WO | WO-2009/155283 A2 | 12/2009 |

OTHER PUBLICATIONS

Dayam, Chem MEd Chem, VOl 1(2), pp. 238-244, 2006.*
Ukrainets, Chem Het Compounds, VOl 43(1), pp. 63-66, 2007.*
Ukrainets, Chem of Het compounds, VOl 43(12), pp. 1532-1539, 2007.*
International Search Report for Application No. PCT/IB2011/055098, dated Apr. 4, 2012.
Ahn, S, et al., In Vivo *Analysis of Quiescent Adult Neural Stem Cells Responding to Sonic Hedgehog*, Nature, vol. 437, No. 7060 (2005) pp. 894-897.
Angot, E., et al., *Chemoattractive Activity of Sonic Hedgehog in the Adult Subventricular Zone Modulates the Number of Neural Precursors Reaching the Olfactory Bulb*, Stem Cells, vol. 16, No. 9 (2008) pp. 2311-2320.
Beachy, P.A., et al., *Tissue Repair and Stem Cell Renewal in Carcinogenesis*, Nature vol. 432, No. 7015 (2004) pp. 324-331.
Berman, D.M., et al., *Medulloblastoma Growth Inhibition by Hedgehog Pathway Blockage*, Science vol. 297, No. 5586 (2002) pp. 1559-1561.

(Continued)

*Primary Examiner* — D M Seaman
(74) *Attorney, Agent, or Firm* — Alston & Bird LLP

(57) ABSTRACT

The present invention relates to the use of quinolinone derivatives of general formula (I), ligands of the Smo receptor or of related receptors which target a binding site of the receptor which is different from the known ligand binding sites, as research tools for identifying modulators of the Smo receptor or of related receptors, characterizing the Hedgehog signalling pathway and diagnosis; the invention also relates to kits containing said derivatives of general formula (I).

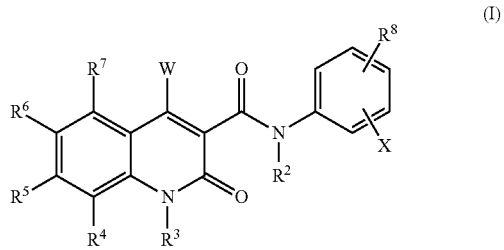

(I)

11 Claims, 4 Drawing Sheets

(56) References Cited

OTHER PUBLICATIONS

Brunton, S.A., et al., *Potent Agonists of the Hedgehog Signaling Pathway*, Bioorg Med Chem Lett, vol. 19, No. 15 (2009) pp. 4308-4311.

Charytoniuk, D.E., et al., *Intrastriatal Sonic Hedgehog Injection Increase Patched Transcript Levels in the Adult Rat Subventricular Zone*, Eur J Neurosci vol. 16, No. 12 (2002) pp. 2351-2357.

Chen, B., et al., *Small Molecule-mediated disruption of Wnt-dependent Signaling in Tissue Regeneration and Cancer*, Nat Chem Biol, Bol 5, No. 2 (2009) pp. 100-107.

Chen, J.K, et al., *Small Molecule Modulation of Smoothened Activity*, Proc Natl Acad Sci USA, vol. 99, No. 22 (2002) pp. 14071-14076.

Corcoran, R.B., et al., *Oxysterols Stimulate Sonic Hedgehog Signal Transduction and Proliferation of Medulloblastoma Cells*, Proc Natl Acad Sci USA, vol. 103, No. 22 (2006) vol. 103, No. 22 (2006) pp. 8408-8413.

Coulombe, J., et al., *Hedgehog Interacting Protein in the Mature Brain: Membrane-Associated and Soluble Forms*, Mol Cell Neurosci, vol. 25, No. 2 (2004) pp. 323-333.

Frank-Kamenetsky, M., et al., *Small Molecule Modulators of Hedgehog Signaling: Identification and Characterization of Smoothened Agonists and Antagonists*, J Biol, vol. 1, No. 2 (2002) p. 10.

Ho, K.S., et al., *Sonic Hedgehog in the Nervous System: Functions, Modifications and Mechanisms*, Curr Opin Neurobiol, vol. 12, No. 1, (2002) pp. 57-63.

Incardona, J.P, et al., *The Teratogenic Veratrum Alkaloid Cyclopamine Inhibits Sonic Hedgehog Signal Transduction*, Development, vol. 125, No. 18 (1998) pp. 3553-3562.

Ingham, P.W. et al., *Hedgehog Signaling in Animal Development: Paradigms and Principles*, Genes Dev, vol. 15, No. 23 (2001) pp. 3059-3087.

Josef, J., et al, *Ring-substituted 4-Hydroxy-1H-quinolin-2-ones: Preparation and Biological Activity*, Molecules, vol. 14, No. 3 (2009) pp. 1145-1159.

Lai, K., et al., *Sonic Hedghog Regulates Adult Neural Progenitor Proliferation in Vitro and in Vino*, Nat. Neurosci, vol. 6, No. 1 (2003) pp. 21-27.

Linnan, H., et al., *Probabilistic Neural Network Multiple Classifier System for Predicting and Quinoline Derivatives*. Chemical Research in Toxicology, vol. 18, No. 3 (2005) pp. 428-440.

Loulier, K., et al., *Increase of Proliferating Oligodendroglial Progenitors in the Adult Mouse Brain upon Sonic Hedgehog Delivery in the Lateral Ventricle*. J Neurochem, vol. 98, No. 2 (2006) pp. 530-542.

Lum, L., et al., *The Hedghog Response Network: Sensors, Switches, and Routers*, Science, vol. 34, No. 5678 (2004) pp. 1755-1759.

Ma, G., et al., *Recent Progress in the Study of Hedgehog Signaling*, J Genet Genomics, vol. 35, No. 3 (2008) pp. 129-137.

May, Y., et al., *Hedghog-Medicated Patterning of the Mammalian Embryo Requires Transporter-Like Funcation of Dispatched*, Cell, vol. 111, No. 1 (2002) pp. 63-75.

Marti, E., et al., *Sonic Hedgehog in CNS Development: One Signal, Multiple Outputs*, Trends Neurosci., vol. 25, No. 2 (2002) pp. 89-96.

McMahon, A.P., et al., *Development Roles and Clinical Significance of Hedgehog Signaling*, Curr Top Dev Biol, vol. 53 (2003) pp. 1-114.

Pepinsky, R.B., et al., *Long-acting Forms of Sonic Hedghog with Improved Pharmacokinetic and Pharmacodynamic Properties are Efficacious in a Nerve Injury Model*, J Pharm Sci, vol. 91, No. 2, (2002) pp. 371-387.

Pepinsky, R.B., et al., *Identification of a Palmitic Acid-Modified Form of Human Sonic Hedgehog*, J Biol Chem, vol. 273, No. 22 (1998) pp. 14037-14045.

Rohatgi, R., et al., *Patched1 Regulates Hedgehog Signaling at the Primary Cilium*, Science vol. 317, No. 5836 (2007) pp. 372-376.

Romer, J.T., et al., *Suppression of the Shh Pathway Using a Small Molecule Inhibitor Eliminates Medulloblastoma in Ptc1 (+/−) p53(−/−) Mice*, Cancel Cell, vol. 6, No. 3 (2004) pp. 229-240.

Rominger, C.M., et al., *Evidence for Allosteric Interactions of Antagonist Binding to the Smoothened Receptor*, J Pharmacol Exp Ther, vol. 329, No. 3 (2009) pp. 995-1005.

Scales, S.J., et al., *Mechanisms of Hedgehog Pathway Activation in Cancer and Implications for Therapy*, Trends Pharmacol Sci, vol. 30, No. 6 (2009) pp. 303-312.

Sinha, S., et al., *Purmorphamine activates the Hedgehog Pathway by Targeting Smoothened*, Nat Chem Biol, vol. 2, No. 1 (2006) pp. 29-30.

Stecca, B., et al., *A GLI1-p53 Inhibitory Loop Controls Neural Stem Cell and Tumor Cell Numbers*, Embo J, vol. 28, No. 6 (2009) pp. 663-676.

Taipale, J., et al., *Effects of Oncogenic Mutations in Smoothened and Patched can be Reversed by Cyclopamine*, Nature, vol. 406, No. 6799 (2000) pp. 1005-1009.

Taipale, J., et al., *Patched Acts Catalytically to Suppress the Activity of Smoothened*, Nature vol. 418, No. 6900 (2002) pp. 892-897.

Traiffort, E., et al., *Discrete Localizations of Hedgehog Signaling Components in the Developing and Adult Rat Nervous System*, Eur J Neurosci, vol. 11, No. 9 (1999) pp. 3199-3214.

Traiffort, E., et al., *Functional Characterization of Sonic Hedgehog Mutations Associated with Holoprosencephaly*, J Biol Chem, vol. 279, No. 41 (2004) pp. 42889-42897.

Traiffort, E., et al., *High Expression and Anterograde Axonal Transport of Aminoterminal Sonic Hedgehog in the Adult Hamster Brain*, Eur J Neurosci, vol. 14, No. 5 (2001) pp. 839-850.

Tsuboi, K., et al., *Intrastriatal Injection of Sonic Hedgehog Reduces Behavioral Impairment Disease*, Exp Neurol, vol. 173, No. 1 (2002) pp. 95-104.

Ukrainets, I.V., et al., *4-Hydroxy-2-quinoles 138. Synthesis and study of structure-biological activity relationships in a series of 1-hydroxy-3-oxo-5, 6-dihydro-3H-pyrrolo [3,2,1-ij]iquinolone-2-carboxylic acid anilides*, Chemistry of Heterocyclic Compounds, vol. 43, No. 12 (2007) pp. 1532-1539.

Varjosalo, M., et al., *Hedgehog: Functions and Mechanisms*, Genes Dev, vol. 22, No. 18, (2008) pp. 2454-2472.

Wang, Y., et al., *Selective Translocation of Intracellular Smoothened to the Primary Cilium in Response to Hedgehog Pathway Modulation*, Proc Natl Acad Sci USA, vol. 106, No. 8 (2009).

Wechsler-Reya, R., et al., *The Developmental Biology of Brain Tumors*, Annu Rev Neurosci, vol. 24 (2001) pp. 385-428.

Wilson, C.W., et al., *Smoothered Adopts Multiple Active and Inactive Conformations Capable of Trafficking to the Primary Cilium*, PLoS One, vol. 4, No. 4 (2009) p. e5182.

Wu, X., et al., *Purmorphamine Induces Osteogenesis by Activation of the Hedgehog Signaling Pathway*, Chem Biol, vol. 11, No. 9 (2004) pp. 1229-1238.

Yang, H., et al., *Converse Conformational Control of Smoothened Activity by Structurally Related Small Molecules*, J Biol Chem, vol. 284, No. 31 (2009) pp. 20876-20884.

Zhao, Y., et al., *Hedghog Regulates Smoothened Activity by Inducing a Conformational Switch*, Nature, vol. 450, No. 7167 (2007) pp. 252-258.

\* cited by examiner

USE OF QUINOLINONE DERIVATIVES AS A RESEARCH TOOL

FIELD

The present invention relates to the use of quinolinone derivatives of general formula (I), which are ligands of the Smo receptor or of related receptors that target a binding site of the receptor which is different from the known ligand binding sites, as research tools for identifying modulators of the Smo receptor or of related receptors, to the characterization of the Hedgehog signaling pathway and to diagnosis; the invention also relates to kits containing said derivatives of general formula (I).

BACKGROUND

Compounds which modulate the Hedgehog pathway, which is the preferred pathway for cell differentiation, have the advantage of being able to be used to promote the differentiation of stem cells of embryonic or adult origin or multipotent cells. The repair of tissues damaged subsequent to a disease, a trauma or age increasingly uses stem cells or progenitor cells which retain the ability to differentiate into various cell types. These cells constitute a reservoir capable of renewing tissues in order to restore biological functions. Mesenchymal stem cells, for example, can give osteoblasts, chondrocytes, adipocytes or hematopoiesis-supporting stromal cells.

The techniques for directing these cells toward a chosen phenotype are generally laborious (transformation of cells using expression vectors and need to express several genes) and alternative solutions such as the use of small synthetic molecules which induce differentiation would constitute a promising track.

The Hedgehog (Hh) signaling molecule is a secreted protein which activates a signaling pathway which plays a fundamental role in the morphogenesis of numerous tissues and the development of the brain, and also in cell proliferation, and appears to be involved in tissue maintenance and repair in adults (Ingham and McMahon 2001; Wechlser-Reya and Scott 2001; Marti and Bovolenta 2002; Lum and Beachy 2004; Varjosalo and Taipale 2008).

Hh proteins are synthesized in the form of immature precursors of approximately 45 kDa which are subjected to an intramolecular cleavage catalyzed by the C-terminal region of the precursor. This cleavage produces a C-terminal fragment of 25 kDa without a known additional function and an active amino-terminal fragment of 19 kDa which has a cholesterol molecule bonded to its C-terminal end. This N-terminal fragment has all the known signaling activities of Hh proteins.

The Hh protein signaling pathway comprises three main components: the Hh ligand, a transmembrane receptor circuit, composed of the Patched negative regulator (Ptc) and the Smoothened activator (subsequently denoted without distinction Smo or Smoothened), and a cytoplasmic complex which regulates the transcriptional effectors.

In mammals, there are two Ptc genes encoding, respectively, Ptc1 and Ptc2, which are glycoproteins comprising 12 transmembrane domains, homologous to bacterial transporters. The product of the Smo gene which encodes a protein of the G protein-coupled receptor family has no known endogenous ligand. The exact mechanism of regulation of the Hedgehog pathway has not yet been completely elucidated. In the absence of Hh, Ptc appears to block the constitutive activity of Smo. The binding of Hh to Ptc appears to lift this inhibition and enable the transduction of the signal by means of Smo. The mechanism of regulation of the activity of Smo by Ptc could involve a molecule which is transported by Ptc and which interacts with Smo (Taipale et al. 2002). Activation of Gli transcription factors is involved in the cascade of events resulting from the activity of Smo. The type I transmembrane protein HIP (Hedgehog Interacting Protein) constitutes another receptor of Hh molecules and constitutes a negative regulator of the pathway (Ho and Scott 2002). Other genes, such as dispatched (DispA), in particular, appear to be involved in the release and accumulation in the extracellular medium of Hh proteins in soluble form (Ma et al. 2002). More recently, other membrane proteins such as Cdo and Boc have been described as capable of binding to Shh and of potentiating its effect (Ma et al. 2008).

The Hh protein and the associated transduction pathway, initially demonstrated in drosophila, are conserved in vertebrates and invertebrates. A single Hh homolog is present in drosophila, whereas three Hh homologs: Sonic (Shh), Indian (Ihh) and Desert (Dhh), are present in mammals. Among these three homologs, Shh has been most commonly studied owing to its widespread expression profile during development. Shh participates in ventralization of the neural tube by specifying the early phenotype of several neuronal types along the ventral median line (spinal cord motoneurons, dopaminergic or cholinergic neurons) and by inducing the generation of oligodendrocyte precursors from the ventral spinal cord (McMahon et al. 2003). Moreover, Shh induces the survival of gabaergic and dopaminergic neurons, directs the fate of serotininergic precursors and prevents dopaminergic neuron deaths caused by the MPP toxin. Finally, it induces the proliferation of granular cell precursors in the early post-natal cerebellum. The other members of the Hh family, for their part, participate respectively in the development of bone tissue (Ihh), of the testicles of peripheral nerves (Dhh). In addition, the results obtained with Shh also apply to Dhh and Ihh.

The regulatory role of the Hedgehog protein signaling pathway during embryonic development has been widely studied: Hh has been associated with the processes for maintaining and repairing normal tissue, and with the spatial temporal regulation of proliferation and differentiation, thus allowing developing tissues to reach their correct sizes with the appropriate cell types and appropriate degrees of vascularization and innervation. The essential role of the function of Hh is demonstrated by the dramatic consequences of defects in this signaling pathway in the human fetus, such as holoprosencephaly observed with Shh mutants (Traiffort et al. 2004).

The Shh pathway has been identified in the spinal cord and the adult brain where the amino-terminal active form of the molecule is expressed in numerous regions, at a level higher than that encountered during the early post-natal period (Traiffort et al. 1999; Traiffort et al. 2001; Coulombe et al. 2004).

Although the roles of Shh in adults have not been completely elucidated, its involvement in the maintenance and renewal of stem cells is increasingly studied (Charytoniuk et al. 2002; Ahn and Joyner 2005; Stecca and Ruiz i Altaba 2009). These stem cells have been identified in several regions of the adult brain, including the subvectricular zone (SVZ) and the subgranular zone (SGZ) of the hippocampus. They provide new precursors throughout life, which have the ability to migrate respectively to the olfactory bulb and the granular cell layer. Under defined pathological conditions, these cells can deviate from their path to the damaged zone. Furthermore, Shh has a chemoattractive activity on neural precursors of the SVZ, an effect which is blocked by an Smo inhibitor (Argot et al. 2008). Shh also stimulates the proliferation of neural progenitors in the SGZ (Lai et al. 2003), but the results remain controversial for those of the SVZ. Moreover, Shh injected into the lateral ventricle of mice also makes it possible to increase the number of oligodendroglial precursors in the cortex, suggesting that activation of the pathway could be of therapeutic interest in demyelinating diseases (Loulier et al. 2006).

Finally, under pathological conditions, such as those observed in a model of Parkinson's disease or a model of peripheral neuropathy, Shh is capable of preserving the axonal projections of dopaminergic neurons in the striatum or of reducing the time necessary for motor recovery subsequent to crushing of the sciatic nerve (Pepinsky et al. 2002; Tsuboi and Shults 2002).

Dysfunctions of the Shh signaling pathway have been associated with many cancers, more particularly with basal cell carcinomas in the skin and with medulloblastomas in the brain. These tumors are most commonly related to mutations of various participants of the Hedgehog pathway, causing an overactivation thereof (Beachy et al. 2004; Scales and de Sauvage 2009). More generally, the location of these tumors is closely correlated with the sites of expression of the components of the pathway during embryonic development. By way of nonlimiting example, mention may be made of: breast cancers, meningiomas, glioblastomas, gastrointestinal cancers (in particular of the stomach), prostate cancers, ovarian fibromas and dermoids, rhabdomyosarcomas, small cell lung cancers, and oral squameous cell carcinomas. Recently, Shh has been associated with psoriasis.

Owing to the crucial role of the Hh protein signaling pathway in many physiological processes and, consequently, the significance of the pathological conditions associated with the dysfunction thereof, the components of this pathway represent targets for the development of new molecules capable of modulating, i.e. of activating or inhibiting, this pathway and therefore of positively or negatively regulating development, including the proliferation, the differentiation, the migration and the survival (apoptosis) and/or the activity of differentiated cells and of stem cells, in vitro and/or in vivo in the embryo or in adults.

Such molecules, in particular inhibiting molecules, are of use in the treatment of tumors associated with hyperactivation of the Hedgehog pathway: nervous tissue tumors (medulloblastomas, primitive neuroectodermal tumors, glioblastomas, meningiomas and oligodendrogliomas), skin tumors (basal cell carcinomas, trichoepitheliomas), muscle and bone tissue tumors (rhabdomyosarcomas, osteosarcomas) and tumors of other tissues (kidney, bladder).

Such molecules, in particular stimulating molecules, are also of use in the treatment of pathological conditions of neurodegenerative type involving the Hh pathway (Parkinson's disease, Huntington's chorea, Alzheimer's disease, multiple sclerosis, motoneuron disease), and diseases in which modulation of the Hh signaling pathway could be beneficial, such as diabetes.

Such molecules are also of use in the medical or surgical treatment (plastic or reconstructive surgery, tissue or organ transplant) of numerous acute, subacute or chronic, genetic or acquired pathological conditions—involving a tissue dysfunction related to a dysregulation of the Hh pathway-, for inducing the formation, regeneration, repair and/or increase in the activity of tissues such as, in a nonlimiting manner: the nervous tissue [central nervous system (brain) and peripheral nervous system (sensory, motor, sympathic neurons)], bone, cartilage, testicles, liver, spleen, intestine, pancreas, kidneys, smooth and squelletial muscles, heart, lungs, skin and body hair, mucus membranes, blood cells and immune system cells. By way of nonlimiting example of these pathological conditions, mention may in particular be made of: neuropathies and associated neuromuscular diseases, diabetes, alopecia, burns, ulcerations (skin and mucosal) and spermatogenesis disorders.

Various molecules, capable of modulating the activity of the Hedgehog pathway, have been identified (the structures of some of these molecules will be represented hereinafter):

the Hh proteins and derived polypeptides which stimulate the pathway by acting on the Ptc protein;

agonists derived from oxysterols (Corcoran and Scott 2006) and smaller organic molecules such as SAG (Chen et al. 2002); the Hh molecules Ag1.2 (Frank-Kamenetsky et al. 2002) or else purmorphamine (Sinha and Chen 2006), the activity of which on the Smo receptor has been established. Recently, more active Ag1.2 derivatives have been described (Brunton et al. 2009);

nitrogenous or non-nitrogenous heterocyclic organic molecules which inhibit the Hedgehog pathway (see international applications WO 2007/054623, WO 2007/059157, WO 01/74344, WO 01/19800, WO 01/26644, WO 02/30421, WO 2005/033288, WO 2005/042700, WO 2008/014291 and WO 2007/120827); a compound of this type is currently in clinical testing (GDC-0449 described from WO 2006/028958);

benzamidazole derivatives (WO 2008/075196);

plant steroids extracted from *Veratrum* spp (cyclopamine, jervine, etc.) and derivatives thereof which inhibit the pathway (see the international patents and applications U.S. Pat. No. 6,432,970, WO 99/52534, WO 01/27135, U.S. Pat. No. 6,291,516, WO 00/41545 and WO 02/30462 and Taipale et al., 2000 and Berman et al. 2002). However, cyclopamine is a teratogenic agent responsible for holoprosencephaly and cyclopia in the embryo in mammals, and an absence of toxicity, for mammals, of the other plant steroid-derived compounds has not yet been demonstrated;

mifepristone (17β-hydroxy-11β-(4-dimethylamino-phenyl)-17α-(prop-1-ynyl)estra-4,9-dien-3-one), also known as RU-486 or RU-38486 (see application FR 03/00646) for which an inhibitory activity on the activity of the Hh protein signaling pathway has been demonstrated;

N-acylthiourea and N-acylurea molecules which inhibit the Hedgehog protein signaling pathway (see application FR 08/02302).

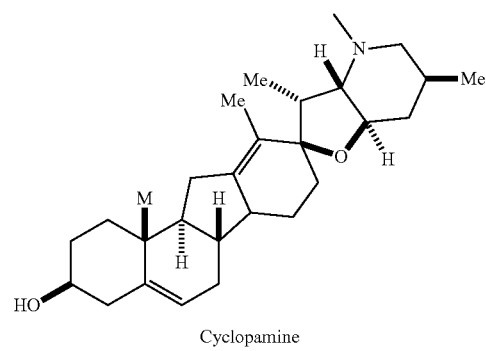

Cyclopamine

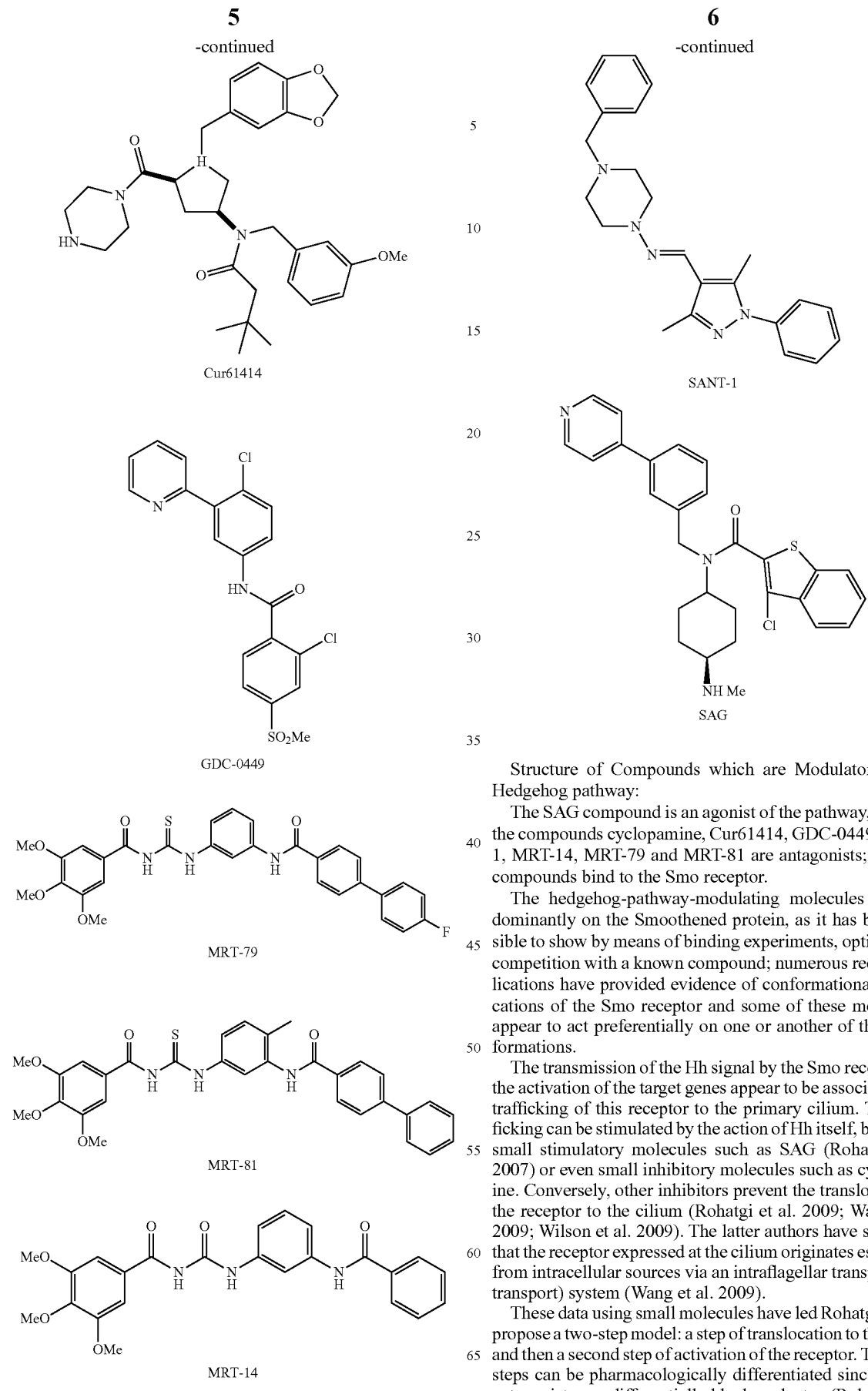

Structure of Compounds which are Modulators of the Hedgehog pathway:

The SAG compound is an agonist of the pathway, whereas the compounds cyclopamine, Cur61414, GDC-0449, SANT-1, MRT-14, MRT-79 and MRT-81 are antagonists; all these compounds bind to the Smo receptor.

The hedgehog-pathway-modulating molecules act predominantly on the Smoothened protein, as it has been possible to show by means of binding experiments, optionally in competition with a known compound; numerous recent publications have provided evidence of conformational modifications of the Smo receptor and some of these modulators appear to act preferentially on one or another of these conformations.

The transmission of the Hh signal by the Smo receptor and the activation of the target genes appear to be associated with trafficking of this receptor to the primary cilium. This trafficking can be stimulated by the action of Hh itself, but also of small stimulatory molecules such as SAG (Rohatgi et al. 2007) or even small inhibitory molecules such as cyclopamine. Conversely, other inhibitors prevent the translocation of the receptor to the cilium (Rohatgi et al. 2009; Wang et al. 2009; Wilson et al. 2009). The latter authors have suggested that the receptor expressed at the cilium originates essentially from intracellular sources via an intraflagellar transport (IFT transport) system (Wang et al. 2009).

These data using small molecules have led Rohatgi et al. to propose a two-step model: a step of translocation to the cilium and then a second step of activation of the receptor. These two steps can be pharmacologically differentiated since various antagonists can differentially block each step (Rohatgi et al.

2009). Similarly, Wilson et al. suggest that Smo exists in several active or inactive conformations which influence its location and its transport to the cilium (Wilson et al. 2009).

From the molecular point of view, Zhao et al. have shown that the inactive form of Smo is maintained by molecular electrostatic interactions maintained by arginine clusters in the cytoplasmic tail. Following the action of Hh, the receptor is phosphorylated and these interactions are disrupted. The conformational change then occurs and induces dimerization of the cytoplasmic tails required for the activation of Smo (Zhao et al, 2007).

These authors suggest that, depending on the number of arginine clusters inhibited by differential phosphorylation, the Smo receptor could operate as a molecular rheostat of Hh signaling.

The conformation of the Smo receptor appears to be particularly linked to the action of pharmacological compounds. It has recently been shown that two known antagonists of the receptor: SANT-1 and SANT-2, act allosterically on distinct sites of the receptor (Rominger et al. 2009). Moreover, it has been published that simply changing a methyl to a propyl or allyl on the SAG agonist makes it possible to convert this molecule into powerful antagonists ($IC_{50}$=20-70 nM, SANT75, SANT74), by regulating the conformation of the Smo receptor (Yang et al. 2009).

SUMMARY

The inventors have identified novel compounds which are quinoline derivatives that activate differentiation; the biological activity induced by these compounds is inhibited by Smo antagonists with different pharmacological characteristics compared with SAG, an Smo agonist, demonstrating that these compounds act on a binding site which is different than that of SAG.

These compounds are defined by the general formula (I) below:

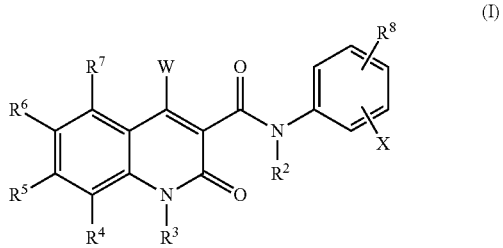

(I)

in which:
X, in the ortho, meta or para position, represents —H, —OH, —$NH_2$, a halogen atom, preferably chlorine or bromine, an alkyl radical consisting of a linear or branched carbon-based chain having from 1 to 10 carbon atoms, an alkoxy radical (of formula —O-alkyl where the alkyl group of the alkoxy radical is as previously defined), a cycloalkyl having from 3 to 8 carbon atoms or an aryl group;
$R^8$, in the ortho, meta or para position, on a carbon other than that which bears the X radical, represents:
(C=O)—NH—$R^1$, —(C=O)—O—$R^1$ or —NH—(C=O)—$R^1$;
W represents —H, —OH, —$NH_2$ or a halogen atom, preferably chlorine or bromine;

$R^1$, $R^2$ and $R^3$, which may be identical or different, and independently of one another, represent:
a hydrogen atom; or
an alkyl group consisting of a linear or branched carbon-based chain having from 1 to 10 carbon atoms, optionally unsaturated with one or more double or triple bonds, and optionally substituted with one or more heteroatoms such as O and S, with one or more halogen atoms or with one or more aryl or heteroaryl groups, preferably a pyridine group; or
a cycloalkyl having from 3 to 8 carbon atoms, optionally substituted with an alkyl radical consisting of a linear or branched carbon-based chain having from 1 to 10 carbon atoms or an alkoxy radical (of formula —O-alkyl where the alkyl group is as previously defined);
$R^4$, $R^5$, $R^6$ and $R^7$, which may be identical or different, and independently of one another, are chosen from —H, —Cl, —Br, —I, —CN, —$NO_2$, an alkyl radical consisting of a linear or branched carbon-based chain having from 1 to 10 carbon atoms, an alkoxy radical (of formula —O-alkyl where the alkyl group is as previously defined) or a cycloalkyl having from 3 to 8 carbon atoms, for example a cyclopropyl, a cyclopentyl or a cyclohexyl;
it being understood that $R^3$ and $R^4$ can be fused so as to form, with the adjacent nitrogen and carbon atoms of the quinoline ring which bears them, a 5- or 6-membered ring.

For the purposes of the present invention, the term "alkyl" is intended to mean a linear or branched, saturated hydrocarbon-based aliphatic group having from 1 to 10 carbon atoms, preferably from 3 to 8 carbon atoms.

The term "branched" means that at least one lower alkyl group having from 1 to 6 carbon atoms, such as a methyl or an ethyl, is borne by a linear alkyl chain.

Preferably, the compounds of general formula (I) are such that the $R^3$ radical is an alkyl radical having from 3 to 8 carbon atoms, such as the hexyl radical; the $R^2$ radical is a hydrogen atom or an alkyl radical having from 1 to 3 carbon atoms; and the $R^4$, $R^5$, $R^6$ and $R^7$ radicals represent a hydrogen atom or an alkyl radical having from 1 to 3 carbon atoms.

The term "halogen atom" is intended to mean a bromine, chlorine, iodine or fluorine atom; the bromine and chlorine designations being preferred.

The term "aryl group" is intended to mean any functional group or constitute derived from at least one aromatic ring; mention may be made of phenyl, benzylcyclobutene, pentalene, naphthalene, benzylphenyl and anthracene groups.

The term "heteroaryl group" is intended to mean any functional group or substitute derived from at least one aromatic ring as defined above and containing at least one heteroatom chosen from P, S, O and N; among heteroaryl groups, mention may be made of furan, pyridine, pyrrole, thiophene, imidazole, pyrazole, oxazole, isoxazole, thiazole, pyridine, pyrazine, pyrimidine, pyridazine, benzofuran, isobenzofuran, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine groups.

The present invention thus relates to the use of compounds of general formula (I) as defined above, as research tools for characterizing the Hedgehog signaling pathway.

By way of compounds of general formula (I), mention may in particular be made, in a nonlimiting manner, of:

propyl 4-(1-hexyl-4-hydroxy-2-oxo-1,2-dihydroquinoline-3-carboxamido)benzoate (compound 1):

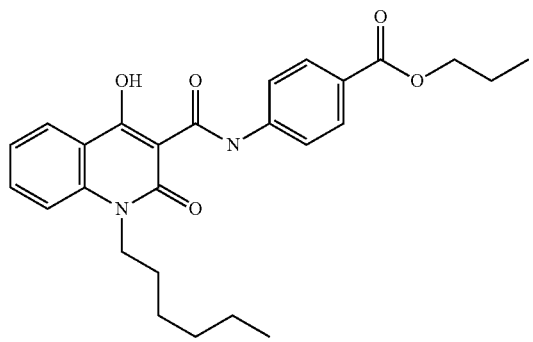 [SMILES: CCCCCCn1c(=O)c(C(=O)Nc2ccc(C(=O)OCCC)cc2)c(O)c2ccccc21]

ethyl 4-(1-benzyl-4-hydroxy-2-oxo-1,2-dihydroquinoline-3-carboxamido)benzoate (compound 2):

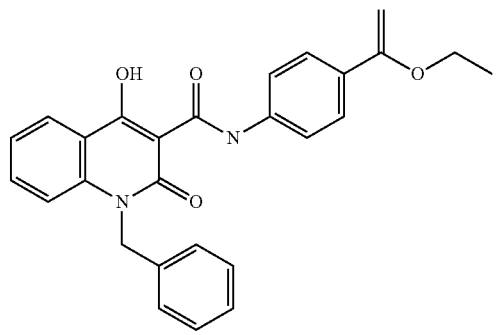 [SMILES: C=C(OCC)c1ccc(NC(=O)c2c(O)c3ccccc3n(Cc3ccccc3)c2=O)cc1]

ethyl 4-(1-hexyl-4-hydroxy-2-oxo-1,2-dihydroquinoline-3-carboxamido)benzoate (compound 3):

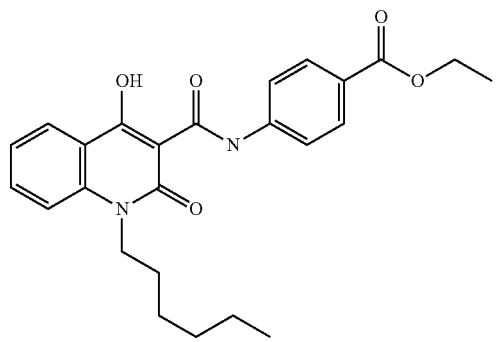 [SMILES: CCCCCCn1c(=O)c(C(=O)Nc2ccc(C(=O)OCC)cc2)c(O)c2ccccc21]

4-(1-hexyl-4-hydroxy-2-oxo-1,2-dihydroquinone-3-carboxamido)benzoic acid (compound 4):

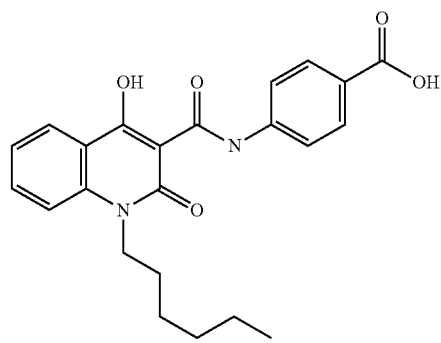 [SMILES: CCCCCCn1c(=O)c(C(=O)Nc2ccc(C(=O)O)cc2)c(O)c2ccccc21]

butyl 4-(1-hexyl-4-hydroxy-2-oxo-1,2-dihydroquinoline-3-carboxamido)benzoate (compound 5):

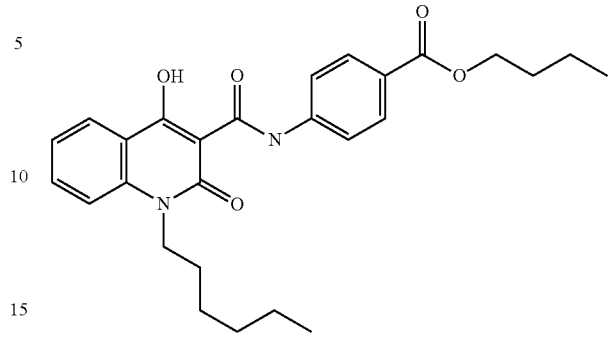

tert-butyl 4-(1-hexyl-4-hydroxy-2-oxo-1,2-dihydroquinoline-3-carboxamido)benzoate (compound 6):

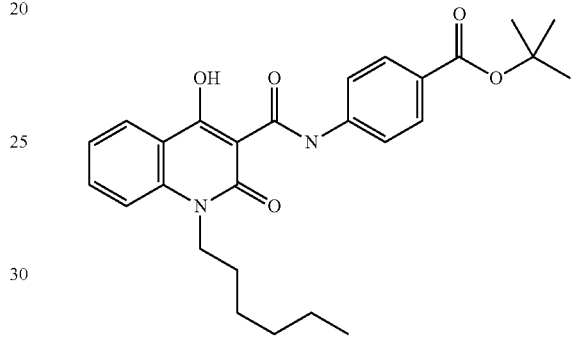

benzyl 4-(1-hexyl-4-hydroxy-2-oxo-1,2-dihydroquinoline-3-carboxamido)benzoate (compound 7):

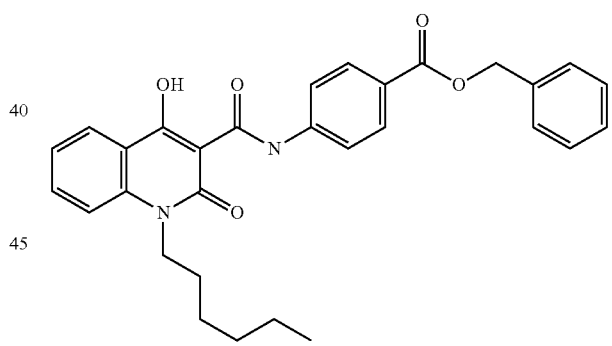

N-(4-butylcarbamoyl)phenyl)-1-hexyl-4-hydroxy-2-oxo-1,2-dihydroquinoline-3-carboxamide (compound 8):

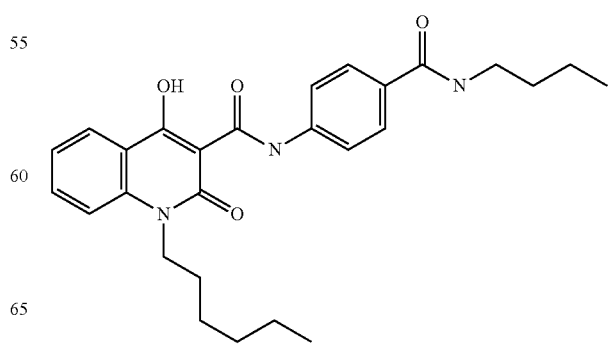

isopropyl 4-(1-hexyl-4-hydroxy-2-oxo-1,2-dihydroquinoline-3-carboxamido)benzoate (compound 9):

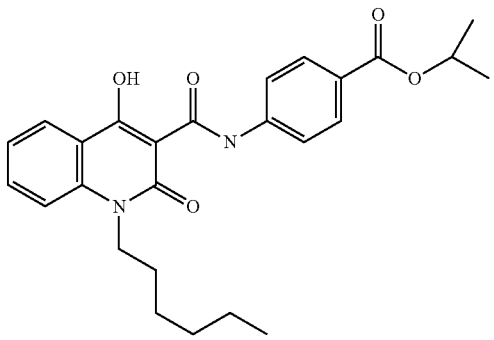 [SMILES: CCCCCCn1c(=O)c(C(=O)Nc2ccc(C(=O)OC(C)C)cc2)c(O)c2ccccc21]

The compounds of general formula (I) in accordance with the invention can be prepared according to the synthesis scheme represented in FIG. 1.

In accordance with the synthesis scheme of FIG. 1, in a first step, an aniline is condensed with triethyl methane tricarboxylate under microwave irradiation so as to obtain quinolinone carboxylates; next, the quinolones are condensed with 4-tert-butylaniline under microwave irradiation so as to give carboxamido-quinolinone esters; the next step consists in saponifying the ester function of these compounds so as to give an acid, which is the starting point for various modifications as illustrated in the experimental examples.

In what follows, the site of the Smo receptor on which SAG binds is called Smo1 and that on which the compounds of general formula (I) bind is called Smo2.

In addition, these compounds of general formula (I) can act on the Hh protein signaling pathway or on other pathways involved in maintaining or differentiating multipotent or totipotent cells: Wnt, Nocht, TGF-β or BMP pathways, for example.

These compounds therefore prove to be highly useful as tools both for discovering new modulators of these signaling pathways and for detecting various forms of the Smo receptor or of related receptors and identifying molecules capable of modulating these various forms.

Various methods for screening for modulators of the Hedgehog pathway are known:
  methods using cell responses of lines or primary cultures: cell differentiation (C3H10T1/2), cell proliferation (primary granular cells of the cerebellum) (see the examples implemented hereinafter);
  methods using competition with a fluorescent compound which acts on the transmembrane domains of the targeted receptor (Bodipycyclopamine) (US 2007/0218775);
  methods using a reporter gene of the pathway implicated (Taipale et al. 2000, Nature, 406, 1005-9);
  an assay detecting Hh activity by measuring Ptc-Hh interactions in the presence or absence of test compound (US 2005/0282231);
  an assay using cells defective for Sufu and a reporter for identifying inhibitors of the Hh pathway acting downstream of Smo (WO 2006/080894).

The present invention thus relates to the use of at least one compound of general formula (I) as a research tool, in particular for identifying molecules capable of interacting with Smoothened by binding to the Smo2 binding site.

In particular, the present invention relates to a method for screening for and/or identifying ligands of the Smo2 binding site of the Smoothened receptor, comprising the steps of:

a) bringing the Smoothened receptor and at least one compound of general formula (I) into contact so as to obtain an [Smo-compound of general formula (I)] complex;
 b) bringing the Smoothened receptor, said compound of general formula (I) and a test molecule into contact;
 c) detecting an interaction between said Smoothened receptor and said test molecules by comparing the Smoothened receptor recovered in step b) with the [Smo-compound of general formula (I)] complex; and
 d) selecting said test molecules for which an interaction, with the Smoothened receptor is measured.

Step a) can be carried out with cells expressing the Smoothened receptor or with extracts of membranes comprising the functional Smoothened receptor; they can in particular be extracts of yeast membranes bearing the functional human Smoothened receptor, capable of being obtained with the process described by Rivoyre et al. (FEBS Letters 579, 2005, 1529-1533).

When step a) is carried out with cells expressing the Smoothened receptor, the expression of said receptor is either constitutive (the receptor is naturally expressed by the cell) or else it results from the transformation of a cell so that it expresses or overexpresses a Smoothened receptor of the same species or of a different species. This Smoothened receptor can also bear a mutation which gives it biochemical or pharmacological properties that are different than the wild-type receptor.

Any compound of general formula (I) can be used for carrying out the method according to the invention; it may, however, be chosen by those skilled in the art in particular according to its affinity for the Smoothened receptor.

Step a) can be carried out in the liquid phase or on a suitable solid support; those skilled in the art will select and adapt these modes of implementation, for example, according to whether they use the Smoothened receptor in the form of membrane extracts or in the form of purified protein.

When step a) is carried out in the liquid phase, the liquid-phase screening method can be carried out according to the following steps:
 a) bringing the Smoothened receptor and at least one compound of general formula (I) into contact so as to obtain an [Smo-compound of general formula (I)] complex;
 b) bringing the Smoothened receptor, said compound of general formula (I) and a test molecule into contact;
 c) recovering said Smoothened receptor possibly bound to one or more test molecules and/or to said compound of general formula (I);
 d) detecting an interaction between said Smoothened receptor and said test molecules by comparing the Smoothened receptor recovered in step c) with the [Smo-compound of general formula (I)] complex; and
 e) selecting said test molecules for which interaction is measured.

Step a) can be carried out with membrane extracts comprising the Smoothened receptor which are then incubated with the compound of general formula (I) and the test molecules; the mixture is then centrifuged; the pellet obtained after centrifugation is resuspended in buffer and is then centrifuged again in order to remove the nonspecific interactions. The binding of test molecule to the Smoothened receptor is then analyzed either by measuring fluorescence, or by measuring radioactivity, depending on the labeling of the compound of general formula (I):
  according to one variant of the liquid-phase screening method, said compound of general formula (I) is prelabeled. The labeling may be radioactive by incorporation of radioactive isotopes such as $^{3}$H, $^{11}$C, $^{14}$C, $^{32}$P, $^{35}$S, $^{125}$I, $^{99m}$Tc, $^{18}$F, $^{64}$Cu, $^{76}$Br, $^{124}$I, $^{13}$N, $^{15}$O or else $^{123}$I according to the conventional methods of the prior art. The labeling of the compound of general formula (I) can also consist of the binding of a fluorophore to said compound according to the methods known to those skilled in the art; the labeling can be detected conventionally using radio imagers selected according to the radioactive atom to be detected, or by measuring the fluorescence. In that case, step d) of detecting the interaction between the Smoothened receptor and one or more test molecules is carried out by comparing the labeling (by radioactivity or fluorescence) of the Smoothened receptors recovered in step c) with that of the [Smo-compound of general formula (I)] complex; the molecules selected are those for which the labeling of the Smoothened receptors recovered in step c) is weaker than that of the [Smo-compound of general formula (I)] complex;

according to another variant of the liquid-phase screening method, the detection of the interaction is carried out by chromatography by comparing the position of the [Smo-compound of general formula (I)] complex with that of the Smoothened receptor recovered in step c); if the position is identical, then there is no interaction between the Smoothened receptor and the test molecule; conversely, a difference in position indicates an interaction; it is then advisable to confirm that the interaction between the test molecule and the Smoothened receptor indeed occurs on the Smo2 binding site.

Step a) of the screening method according to the invention can alternatively be carried out on a suitable solid support.

The term "solid support" is intended to mean in particular a biosensor consisting of a membrane which comprises a biological entity, such as an enzyme, an antibody, a peptide, a microorganism, a biological tissue, a lipid, a nucleic acid, etc., which allows binding with a test molecule, and a transducer which makes it possible to transform the biological signal, such as the binding of a ligand to a protein receptor, into a measurable physical signal, for example an electrochemical (amperometric, potentiometric, conductimetric), optical (light), piezoelectric or calorimetric signal. In the present case, the biological entity bound on the membrane is the Smoothened receptor; in two experiments conducted in parallel, the Smoothened receptor on a solid support is brought into contact with a compound of general formula (I) and with the mixture of said compound of general formula (I) and of a test molecule, the signals obtained in each of these experiments are compared, and the molecules which induce a modification of the signal are selected.

By way of example, the solid support is a biosensor for detecting binding by Plasmon resonance, the use of which makes it possible to visualize and characterize (affinity, association and dissociation constants) interactions between a protein and its ligand via a change in mass at the surface of the biosensor. This change in mass is measured via variations in the angle of plasmon resonance at the surface of the biosensor and does not require a radiolabeled or fluorescent ligand.

When the screening method on a solid support is carried out with membrane extracts comprising the Smoothened receptor, these extracts can be bound by injection onto a lipophilic biosensor. When a lipophilic biosensor is used, the membrane extracts bind to the lipophilic groups bonded, via covalent bonds, to dextran, which makes it possible to follow the interaction between membrane receptors and ligands (Pourshafie M R, Marklund B-I and Ohlson S (2004) *Binding interactions of Escherichia coli with globotetraosylceramide (globoside) using a surface Plasmon resonance biosensor*. J. Microbiol. Meth., 58, 313-320; Wikstrom A and Deinum J (2007) *Probing the interaction of coagulation factors with phospholipid vesicle surface plasma resonance*. Anal. Biochem. 362, 98-107).

Thus, according to a variant of the invention, the biosensor for detecting binding by Plasmon resonance is a lipophilic biosensor such as a Biacore "sensorchip L1" hydrophobic biosensor (GE Healthcare) on which a preparation of membranes containing the Smoothened receptor is bound by injection.

When the screening method on a solid support is carried out with the purified Smoothened receptor, said receptor can also be bound to a biosensor for measuring surface Plasmon resonance which consists in detecting a variation in the index of the interface on which the receptor is bound, when a ligand binds to said receptor.

According to one embodiment variant, the screening method on a solid support also makes it possible to identify Smoothened receptor ligands which do not bind to the Smog binding site; the activating or inhibiting action of these ligands can be characterized by the methods which follow.

The present invention also relates to a method for identifying Smoothened receptor agonists, in particular those which bind to the Smo2 binding site, which, in addition to the steps described for the ligand identification method, comprises the additional steps of bringing the ligand identified into contact with a cell which exhibits a cellular response following the activation of the Smoothened receptor and of selecting the agonist molecules capable of inducing said cellular response of said cell.

The cells which exhibit a cellular response following the activation of the Smoothened receptor are chosen from lines or primary cultures, mesenchymal cells (for example, C3H10T1/2) which respond to activation of the Smoothened receptor by cell differentiation measurable via alkaline phosphatase activity; primary granular cells of the cerebellum which respond to activation of the Smoothened receptor by cell proliferation; stem cells of the adult brain or neural progenitors or else progenitor cells present in the tissues during development or in adults, for which the cellular response can, for example, consist of induction of the genes such as those encoding the transcription factors of the Gli family, or else encoding Patched or Hip, which are genes activated by the Hedgehog pathway.

In particular, the method for identifying agonists according to the invention may be carried out by evaluating, as cellular response, the induction of phosphatase activity by test compounds in the presence of forskolin (see part 2 of example II, where it is shown that compound 1, like SAG, is capable of stimulating osteogenesis); it being possible for compound 1 (agonist) to serve as a positive control for induction of phosphatase activity.

The present invention also relates to a method for identifying a Smoothened receptor antagonist molecule, comprising the following steps:
  a) culturing cells which exhibit a cellular response following the activation of the Smoothened receptor with at least one compound of general formula (I) so as to induce said cell response;
  b) bringing the cells obtained at the end of step a) into contact with a test molecule;
  c) selecting the molecules which induce an inhibition of said cellular response of said cells.

An example of this method is illustrated in the experimental section (example II) which follows.

The molecule for which it is desired to test the Smoothened receptor antagonist activity can in particular be a ligand which binds to the Smo2 binding site of Smoothened, identified by any one of the preceding methods for identifying a ligand according to the invention.

This same method can also be used for identifying molecules capable of inducing a potentiation of the Smoothened receptor activation induced by the compound of general formula (I); the term "potentiation" is intended to mean the ability of a molecule to increase the degree of activation induced by the compound of general formula (I). The molecules which induce an increase in the cellular response of the cells which exhibit a cellular response following the activation of the Smoothened receptor will therefore be selected.

The present invention also relates to a kit for carrying out the methods according to the invention, comprising at least the functional Smoothened receptor and at least one compound of general formula (I). The functional Smoothened receptor is either present in the form of a membrane extract, or in cells which exhibit a cellular response following the activation of the Smoothened receptor.

The experiments comprising binding between the Smoothened receptor and a compound of general formula (I) can also be used for characterizing and identifying:
 new cell types expressing the Smoothened receptor in a conformation where the Smo2 binding site is active;
 or else receptors involved in differentiation, such as receptors related to the Smoothened receptor.

The invention then relates to a method for identifying cells, such as tumor cells, expressing the Smoothened receptor, comprising the steps of:
 a) bringing a test cell into contact with a labeled compound of general formula (I);
 b) cleaning the cells in order to remove said labeled compound of general formula (I) which has not bound to any receptor of said test cell;
 c) detecting the labeled cells.

The compounds can also be used for identifying and characterizing new receptors or new forms of receptors involved in cell differentiation, proliferation, cell death, migration, or cell survival, or else which allow the cell to acquire a property or a state that it has not yet achieved.

According to another variant of the invention, the compounds of general formula (I) are used as a research tool for studying the consequences of the activation of the Smoothened receptor on the Smog binding site. Such studies can, for example, consist in comparing the profile of expression of messenger RNAs and/or of proteins by cells before and after activation by bringing into contact with a compound of general formula (I); the study may further consist of the comparison of the profiles of expression of messenger RNAs and/or of proteins of two groups of cells derived from one and the same cell type, one group of cells having been activated with a compound of general formula (I), the other with an Smo agonist known to bind to a binding site other than Smo1.

The mRNA quantification methods may be those which make it possible to analyze expression patterns of a family of genes, or else all the genes expressed by the cell; modification of microRNA transcription may also be analyzed.

This biochemical or molecular characterization of cells could be used to identify tumor cells sensitive to the compounds of general formula (I) and, at a subsequent stage, to develop a method for the diagnosis of tumors sensitive to the compounds of general formula (I).

The compounds of general formula (I) may also be used to characterize the biological function of a mutant of the Smo receptor; this characterization can be carried out by transforming cells with a vector for expression of an Smo mutant and observing the effect of a compound of general formula (I) on said cell expressing the Smo mutant.

BRIEF DESCRIPTION OF THE DRAWINGS

In addition to the above arrangements, the invention also comprises other arrangements which will emerge from the following description, which refers to examples of demonstrations of the pharmacological properties of the compounds of general formula (I) according to the present invention, and also to the appended drawings in which.

DETAILED DESCRIPTION

Example 1

Figure 1:
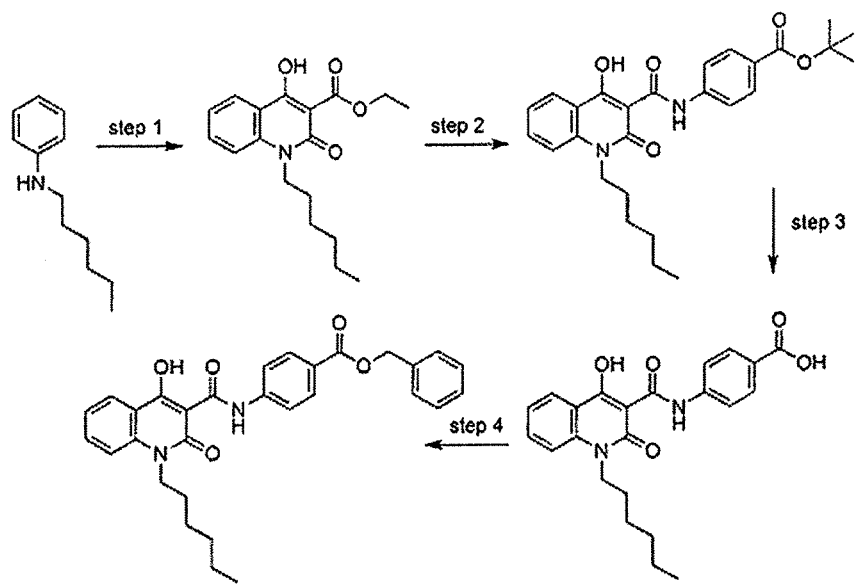
FIG. 1 represents the synthesis scheme for the compounds of general formula (I).

Synthesis of Various Compounds of General Formula (I)

Preparation of ethyl 1-hexyl-4-hydroxy-2-oxo-1,2-dihydroquinoline-3-carboxylate

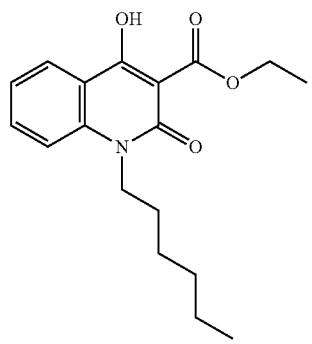 [SMILES: CCCCCCn1c(=O)c(C(=O)OCC)c(O)c2ccccc21]

In a round-bottomed flask equipped with a condenser, N-hexylaniline (355 mg, 2 mmol) is added to a solution of methanetricarboxylic acid triethyl ester (1.35 ml, 6.4 mmol). The resulting reaction mixture is placed in a CEM Discovery microwave oven and irradiated in the open round-bottomed flask, and then the ethanol formed is distilled off (the parameters are the following: power=250 W, temperature=225° C., execution time=5 min, hold time=15 min).

After the microwave heating, the reaction crude is purified on a chromatography column, with petroleum ether: ethyl acetate at 4:1. The crystalline product obtained is dried to give the compound: yield=430 mg (69%). $^1$H NMR (CDCl$_3$): δ 8.16 (d, J=8 Hz, 1H), 7.64 (m, 1H), 7.27-7.19 (m, 2H), 4.48 (q, J=8 Hz, 2H), 4.18 (t, J=8 Hz, 2H), 1.72-0.86 (m, 14H).

I.A. tert-Butyl 4-(1-hexyl-4-hydroxy-2-oxo-1,2-dihydroquinoline-3-carboxyamido)benzoate (compound 6)

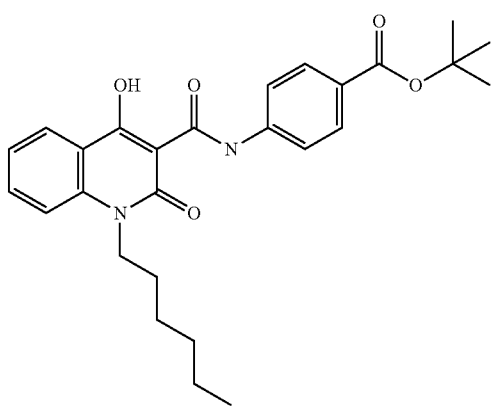 [SMILES: CCCCCCn1c(=O)c(C(=O)Nc2ccc(C(=O)OC(C)(C)C)cc2)c(O)c2ccccc21]

Ethyl 1-hexyl-4-hydroxy-2-oxo-1,2-dihydroquinoline-3-carboxylate (159 mg, 0.5 mmol) and tert-butyl 4-amino-benzoate (193 mg, 1 mmol) are suspended in anhydrous toluene (4 ml) and microwave-heated with the container open (the parameters are the following: power=200 W, temperature=120° C., execution time=7 min, hold time=10 min).

At the end of the reaction, ⅔ of the solvent are evaporated off without a condenser. The reaction crude is purified by means of a chromatographic column, using 4:1 petroleum ether: ethyl acetate. The crystalline product obtained is dried to give the title compound: yield=195 mg (84%), $^1$H NMR (DMSO): δ 8.16 (d, J=8 Hz, 1H), 7.90-7.75 (m, 6H), 7.38 (m, 1H), 4.25 (bs, 2H), 1.60 (bs, 2H), 1.52 (s, 9H), 1.39 (bs, 2H), 1.28 (bs, 5H), 0.84 (bs, 2H).

I.B. 4-(1-hexyl-4-hydroxy-2-oxo-1,2-dihydroquinoline-3-carboxamido)benzoic acid (compound 4)

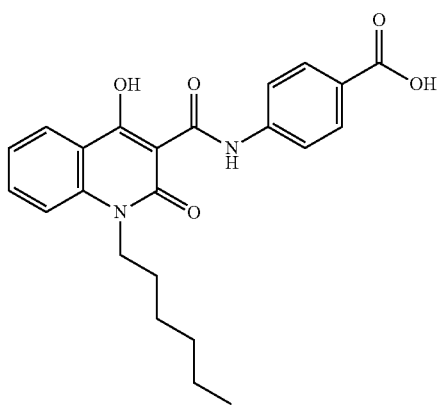 [SMILES: CCCCCCn1c(=O)c(C(=O)Nc2ccc(C(=O)O)cc2)c(O)c2ccccc21]

tert-Butyl 4-(1-hexyl-4-hydroxy-2-oxo-1,2-dihydroquinoline-3-carboxamido)benzoate (83 mg, 0.18 mmol) is added, in fractions, to a solution of trifluoroacetic acid (TFA) cooled to 0° C.; the mixture is left to react for 3 hours. The crude product obtained is washed with ethyl ether until a white crystalline solid forms. The product is dried to give a yield of 61 mg (83%). $^1$H NMR (DMSO): δ 8.16 (d, J=8 Hz, 1H), 7.97-7.65 (m, 6H), 7.38 (m, 1H), 4.27 (bs, 2H), 1.59 (bs, 2H), 1.39 (bs, 2H), 1.28 (bs, 5H), 0.84 (bs, 2H).

I.C. Benzyl 4-(1-hexyl-4-hydroxy-2-oxo-1,2-dihydroquinoline-3-carboxamido)benzoate (compound 7)

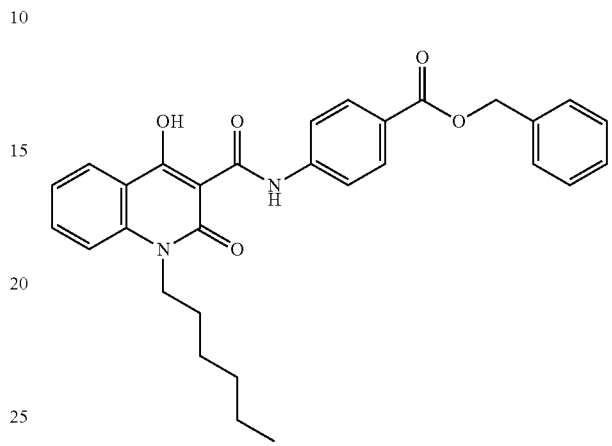

A solution of 4-(1-hexyl-4-hydroxy-2-oxo-1,2-dihydroquinoline-3-carboxamido)benzoic acid (41 mg, 0.1 mmol) in THF is cooled to 0° C., and benzyl alcohol (21 mg, 20 μl, 0.2 mmol) is added, along with EDCI (19 mg, 0.1 mmol) and dimethylaminopyridine (3 mg, 0.02 mmol). The reaction mixture is left to stir overnight. The organic phase is washed with water and evaporated under reduced pressure. The crude product is purified by column chromatography, using 4:1 petroleum ether: ethyl acetate, with a yield of 30 mg (60%). 1H NMR (DMSO): δ 8.16 (d, J=8 Hz, 1H), 8.04 (d, J=8 Hz, 2H), 7.83 (d, J=8 Hz, 3H), 7.68 (d, J=8 Hz, 1H), 7.46-7.25 (m, 6H), 7.38 (m, 1H), 5.30 (s, 2H), 4.28 (bs, 2H), 1.59 (bs, 2H), 1.41-1.15 (m, 6H), 0.84 (bs, 3H).

Example II

Demonstration of the Binding of the Compounds of General Formula (I) to a Specific Binding Site (Smo2) Different than that on which the SAG Compound Acts (Smo1)

The effect of the compounds of general formula (I) according to the invention on the stimulation of differentiation was determined in vitro by analyzing the pluripotent fibroblast cell line C3H10T1/2.

This activation can be inhibited by compounds previously described as Hh pathway antagonist and more specifically Smo receptor antagonist. Moreover, these pharmacological agents have a signal transmission mode distinct from that used by SAG, which is an Hh pathway agonist (Chen et al. 2002).

1) Materials and Methods

Activation of Differentiation by the Compounds of General Formula (I)

The compounds of general formula (I) tested are compounds 1 and 6:

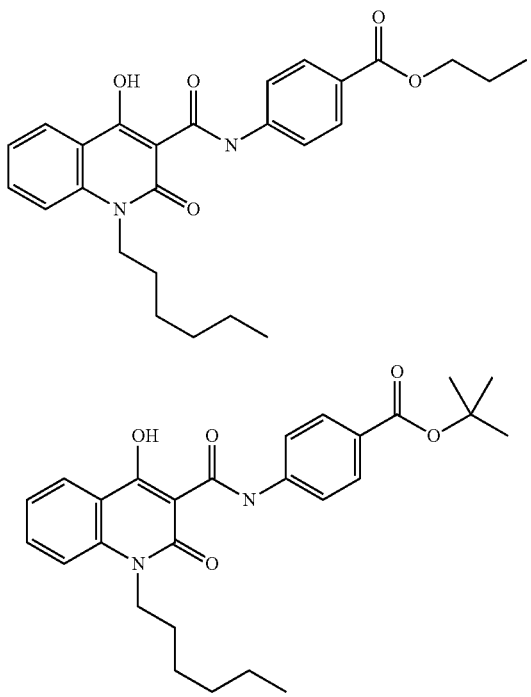

they were dissolved in dimethyl sulfoxide to a concentration of 2.5 mM, and then stored at a temperature of −20° C. until used.

The pluripotent fibroblast cell line C3H10T1/2 (ATCC) was cultured under the conditions recommended by the ATCC. The stimulation of the differentiation of these cells was carried out using increasing concentrations of compounds according to the methods described by Chen et al. and Frank-Kamenetsky et al. (Chen et al. 2002; Frank-Kamenetsky et al. 2002). The activation by the compounds of general formula (I) causes differentiation of the cell line and enables the latter to express alkaline phosphatase. It was thus possible to measure the activity of the compounds via the measurement of alkaline phosphatase activity. By way of comparison, the activity of the SAG compound (Chen et al. 2002), an Smo activator, was tested under the same conditions as those used to test the compounds of general formula (I).

The C3H10T1/2 cells were seeded onto 96-well plates at a density of $5 \times 10^3$ cells per well, 24 hours before the addition of the test compounds at a concentration ranging from 10 nM to 10 μM in DMEM culture medium supplemented with 10% of fetal calf serum. The tests were carried out in quadruplicate. The plates were then incubated for 5-6 days at a temperature of 37° C. under an atmosphere of 5% $CO_2$. The cells were then washed in cold phosphate buffer (phosphate buffered saline: PBS) and then lysed by sonication at 4° C. in 50 μl of a solution containing 0.9% of NaCl and 0.2% of Triton X-100.

The alkaline phosphatase in the resulting lysates was then measured according to the method described by Pepinsky et al. (Pepinsky et al. 1998). After the addition of 100 μm of reaction buffer (200 mM Tris-HCL; pH 10.5; 0.4 M of 2-amino-2-methylpropanol and 8 mM of $MgCl_2$) and of 50 μl of substrate (4 mM of disodium p-nitrophenyl phosphate), the lysates were incubated at 37° C. for 30-60 min and then the optical density was read at a wavelength of 415 nm.

Inhibition of Differentiation by Hedgehog Pathway Antagonists

For the inhibition experiments, compound 1 (1 μM), compound 6 (3 μM) or SAG (0.1 μM) was used to stimulate differentiation in the presence of increasing concentrations (from 0.1 nM to 30 μM) of Smo inhibitors previously described, such as Cur61414 (Frank-Kamenetsky et al. 2002), cyclopamine (Incardona et al. 1998), GDC-0449 (Romer et al. 2004) and also the molecules MRT-14, MRT-79, MRT-80 and MRT-81 (patent application FR 08/02302). These compounds were dissolved in 100% ethanol (Cur61414, cyclopamine) or dimethyl sulfoxide (compounds MRT-14, MRT-79, MRT-80, MRT-81 and GDC-0449) and then stored at −20° C.

Activity of Forskolin and of IWR1

For the experiments in the presence of forskolin, compound 1 (1 μM) and SAG (0.3 μM) were used to stimulate differentiation in the presence of increasing concentrations (1, 3 and 10 μM) of forskolin (Sigma). The IWR1 compound (Sigma), for its part, was used at 10 μM on an activation by compound 1 at 1 μM or SAG at 0.1 μM. The alkaline phosphatase activity was measured as previously.

2) Results 2-1. Activation of Differentiation by Compounds 1 and 6

Figure 2:
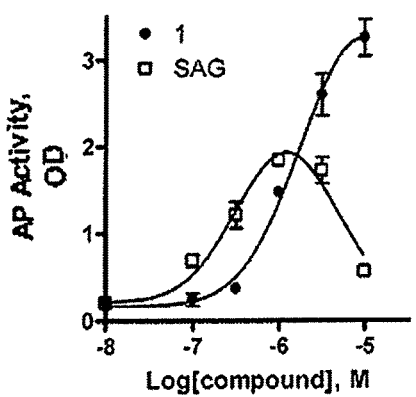
FIG. 2: stimulatory activity of the compounds of general formula (I). Dose-response curve for compound 1 and for SAG on the osteogenic differentiation of C3H10T1/2 cells. The alkaline phosphatase activity, expressed as OD at 415 nm, reflects the differentiation. One experiment with respect to 3-5 carried out.

It was demonstrated that compounds 1 and 6 have the capacity to stimulate osteogenesis in C3H10T1/2 pluripotent cells. This differentiation is linked to the induction of alkaline phosphatase (AP) after 6 days of differentiation. FIG. 2 represents the dose-response curves of compound 1 and of SAG produced in parallel with respect to the stimulation of C3H10T1/2 cells. Compound 1 makes it possible to obtain a maximum stimulation greater than that of the Smo agonist SAG, with a similar affinity.

2-2. Inhibition of the Activity of Compounds 1 and 6 by Smoothened Antagonists

Figure 3:
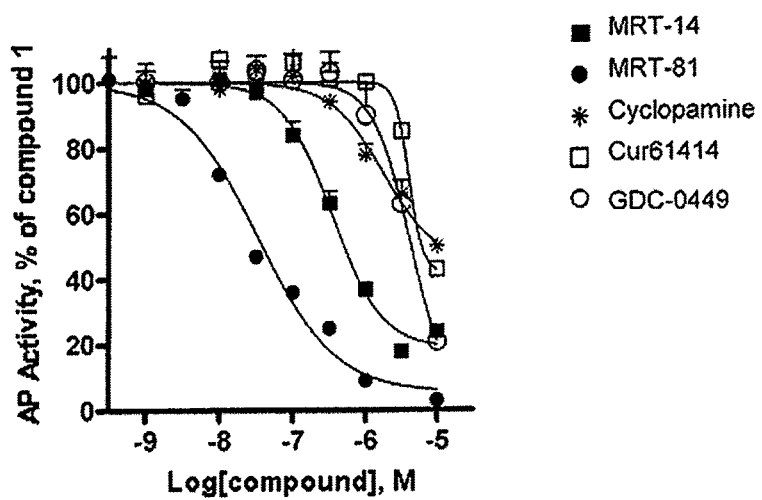
FIG. 3: activity of compound 1 is inhibited by Smo antagonists. C3H10T1/2 cells were incubated for 6 days in the presence of compound 1 (1 µM) and of increasing concentrations of the Hh pathway antagonists indicated.

The activity of compound 1 can be inhibited by Smo receptor antagonists (FIG. 3). It is reflected by a gradual inhibition of the alkaline phosphatase activity induced by compound 1 in the presence of increasing concentrations of known antagonists such as cyclopamine, Cur61414, GDC-0449 or the compounds MRT-14 and MRT-81.

Figure 4:
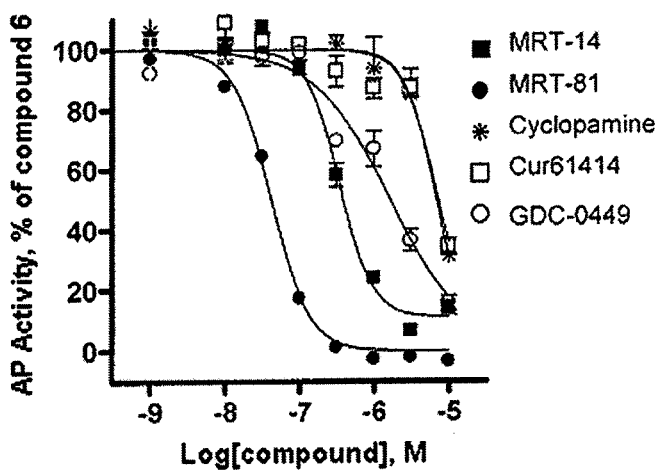
FIG. 4: activity of compound 6 is inhibited by Smo antagonists. The activity of compound 6 (3 µM) was inhibited by the antagonists as indicated in FIG. 2.

Compound 6 also has the characteristic of being able to be inhibited by Smo antagonists (FIG. 4). When the activities of the antagonists tested on the two compounds 1 and 6 are compared, great pharmacological similarity can be noted for these two osteogenesis-stimulating agents. This suggests one and the same mode of action for these compounds.

The affinities of the Smo antagonists for the two compounds 1 and 6 were determined and are reported in table I. They are expressed as $IC_{50}$, which corresponds to the concentration that makes it possible to inhibit 50% of the biological response induced by the agonist compound. The compounds MRT-14 and MRT-81 exhibit good affinity for the response, with extremely close values for the two compounds. The affinities of MRT-14 are, respectively, 0.32 and 0.4 μl for compounds 1 and 6, whereas that of MRT-81 is 0.06 μM for both compounds. Conversely, cyclopamine, Cur61414 and GDC-0449 have little affinity for these compounds ($IC_{50}$=2-10 μM).

TABLE I affinity of Hedgehog pathway antagonists with respect to the
Smo2 sites. The differentiation of the C3H10T1/2 cells is measured
via the alkaline phosphatase activity induced by compounds 1 (1 µM)
and 6 (3 µM). The $IC_{50}$ values are derived from the inhibition
curves as is shown in FIGS. 3 and 4. Mean ± SEN of 2 to
6 independent experiments in quadruplicate.

|  | $IC_{50}$ µM, C3H10T1/2 | |
| --- | --- | --- |
| Antagonist | Compound 1 | Compound 6 |
| MRT-14 | 0.32 ± 0.02 | 0.4 ± 0.1 |
| MRT-81 | 0.06 ± 0.02 | 0.06 ± 0.03 |
| Cyclopamine | 6.6 ± 3.1 | 12 ± 7 |
| Cur61414 | 5.7 ± 1.6 | 7 ± 1 |
| GDC-0449 | 3.4 ± 1.4 | 2 ± 1 |

Compounds 1 and 6 bind to Smo2 binding sites and their binding is blocked by Hedgehog pathway antagonists with the same affinity.

2-3. Comparison of the Activities of the Smoothened Antagonists with Respect to the Smo1 and Smo2 Sites Dose-response curves with respect to the antagonists were also produced in the presence of 0.1 µM of SAG (FIG. 5) in parallel to those performed on compound 1. The SAG compound acts on a binding site called Smo1. The comparison of the pharmacology of the antagonists with respect to these two compounds is given in table II.

When the activities of the Smo antagonists with respect to the stimulation by SAG or by compound 1 are compared, important differences exist both in terms of the maximum inhibitions obtained and the affinities ($IC_{50}$). The first notable difference is the weaker inhibition by cyclopamine, Cur61414 and GDC-0449 observed at 10 µM for compound 1, whereas these compounds enable complete inhibition of the presence of SAG.

Figure 5:
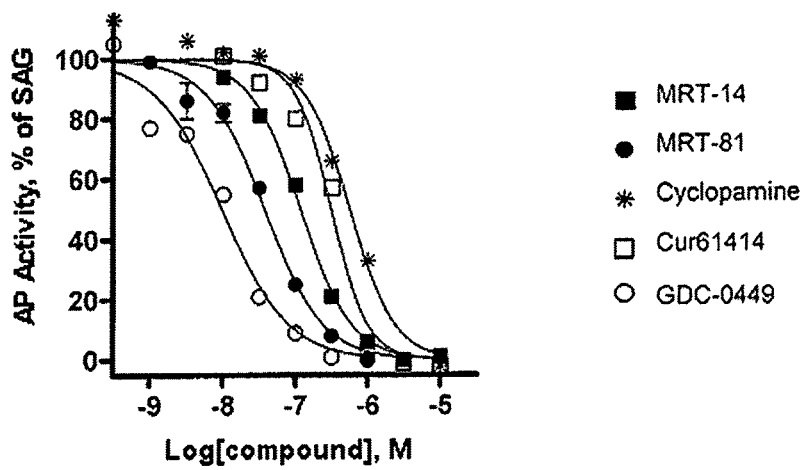
FIG. 5: inhibition of the activity of SAG by the Smo antagonists. The activity of SAG (0.1 µM) was inhibited by the antagonist as indicated in FIG. 2. The SAG compound binds to the Smo1 binding site.

TABLE II comparison of the activity of the Hedgehog pathway antagonists
with respect to the Smo1 and Smo2 sites. The response measuring
the cellular differentiation of mesenchymal stem cells induced
by compound 1 and the SAG compound on C3H10T1/2 cells is measured via
the alkaline phosphatase activity induced by compound 1 (1 µM) and
the SAG compound (0.1 µM). The $IC_{50}$ values are derived from
the inhibition curves as shown in FIGS. 3 and 5 (mean ± SEM
of 2 to 6 independent experiments in quadruplicate).

|  | Smo1 | | Smo2 | |
| --- | --- | --- | --- | --- |
|  | $IC_{50}$, µM | Inhibition 10 µM | $IC_{50}$, µM | Inhibition 10 µM |
| MRT-79 | 0.14 ± 0.06 | 95 | 0.011 ± 0.0 | 100 |
| MRT-81 | 0.06 ± 0.02 | 100 | 05 | 100 |
| SANT-1 | 0.04 ± 0.01 | 100 | 0.06 ± 0.02 | 71 |
| MRT-14 | 0.13 ± 0.05 | 100 | 0.06 ± 0.02 | 95 |
| Cyclopamine | 0.62 ± 0.03 | 98 | 0.32 ± 0.02 | 48 |
|  | 0.33 ± 0.06 | 100 | 6.6 ± 3.1 | 60 |
| Cur61414 | 0.011 ± 0.0 | 100 | 5.7 ± 1.6 | 77 |
| GDC-0449 | 01 |  | 3.4 ± 1.4 |  |

The SAG compound and compound 1 bind, respectively, to the Smo1 and Smo2 binding sites. Their binding is blocked by Hedgehog pathway antagonists (mean±SEM of 2 to 6 independent experiments in quadruplicate).

The compounds MRT-14 and MRT-81 and also the compound SANT-1 exhibit comparable affinities for the Smo1 site (stimulated by SAG) and the Smo2 site (stimulated by compound 1) with similar values. On the other hand, other Hedgehog pathway antagonists are much more selective with respect to Smo1 sites than Smo2 sites (Cur61414, GDC-0449). Conversely, the compounds MRT-81 and MRT-79 are more selective with respect to Smo2 sites than the Smo1 sites. This is explained when the ratio between the $IC_{50}$ values of the compounds obtained with SAG and compound 1 is calculated (table III).

TABLE III selectivity of the Hedgehog pathway antagonists with respect
to Smo1 and Smo2 sites. The $IC_{50}$ values of the antagonists
with respect to the Smo1 sites (stimulated by SAG, 0.1 µM)
and the Smo2 sites (stimulated by compound 1, 1 µM) were evaluated
as in tables I and II (ratio of the means of the $IC_{50}$ values
obtained in 2 to 6 experiments).

| Antagonist | C3H10T1/2 cell differentiation $IC_{50}$ Smo1/$IC_{50}$ Smo2 |
| --- | --- |
| MRT-79 | 0.08 |
| MRT-55 | 0.4 |
| MRT-81 | 0.9 |
| SANT-1 | 1.5 |
| MRT-14 | 2.5 |
| Cyclopamine | 11 |
| Cur61414 | 17 |
| GDC-0449 | 310 |

A selectivity of more than 300-fold is observed with GDC-0449 and of 17-fold with Cur61414 for the Smo1 site compared with the Smo2 site, whereas SANT-1 maintains a similar activity for the Smo1 and Smo2 sites. Conversely, the compounds MRT-81, MRT-55 and MRT-79 are, respectively, 1.3, 2.5 and 12.5 times more selective with respect to Smo2 sites. This specificity of the compounds is significant and demonstrates an important pharmacological difference at the level of the Smo1 and Smo2 binding sites.

2-4. The Smo1 and Smo2 Sites Exhibit Different Activation Mechanisms

Modulation of the Activity of Compound 1 and of SAG by Forskolin

The compounds of general formula (I) and SAG act via distinct pathways. Indeed, it is known that forskolin is an inhibitor of osteogenesis induced by the Hh pathway in mesenchymal stem cells (Wu et al. 2004). The purpose of the tests which follow is to determine whether this characteristic also applies to the compounds of general formula (I).

Figure 6:
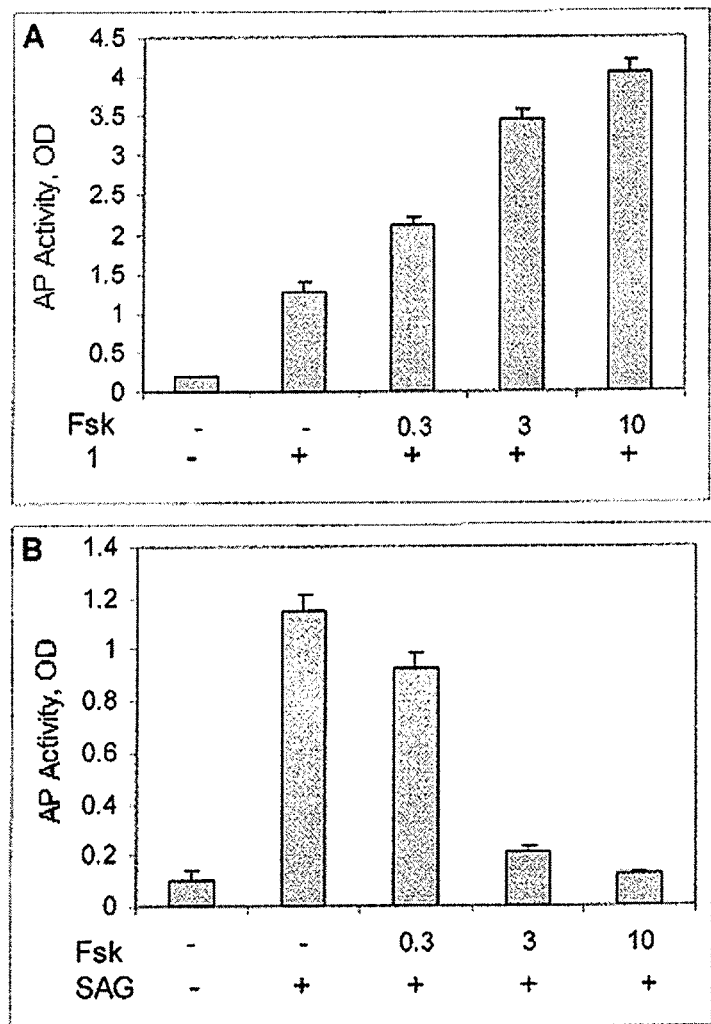
FIG. 6: Forskolin potentiates the response to compound 1 which stimulates the Smog sites and decreases that of SAG which stimulates the Smo1 site. C3H10T1/2 mesenchymal stem cells were treated with compound 1 at 1 µM (A) or SAG at 0.3 µM (B) in the presence of 0.3, 3 or 10 µM of forskolin (Fsk). The alkaline phosphatase enzymatic activity is expressed as OD. A representative experiment with respect to the 3 carried out. Mean±SEM of quadruplicates.

The differentiation of the C3HT10T1/2 cells was stimulated by compound 1 in the presence of forskolin. As demonstrated in FIG. 6, panel (A), it appears that forskolin has a potentiating effect on the response to compound 1, whereas it inhibits the activity of the SAG compound (B). These two osteogenesis-stimulating agents therefore act via distinct pathways. This effect of forskolin was found for other compounds of general formula (I).

Modulation of the Activity of Compound 1 and of SAG by the IWR1 Compound, a Wnt Pathway Antagonist The difference in activity of forskolin on compound 1 and SAG led to a search for other intracellular pathways involved in the activity of the compounds of general formula (I). In addition to the Hh pathway, differentiation of the C3H10T1/2 cells can be stimulated by signaling pathways such as the Wnt, Nocht, TGF-β or BMP pathways, for example. With regard to the Wnt pathway, activation of the canonical pathway induces activation of β-catenin which participates in the activation of the transcription of the TCF/LEF genes. In the absence of Wnt ligands, β-catenin is phosphorylated, and then degraded. Recently, a molecule IWR1 which stabilizes axin2 and leads to the destruction of beta-catenins was discovered (Chen et al. 2009). This inhibitor was used to determine whether axin2 and/or β-catenins could be involved in the transduction of the signal induced by compound 1.

Figure 7:
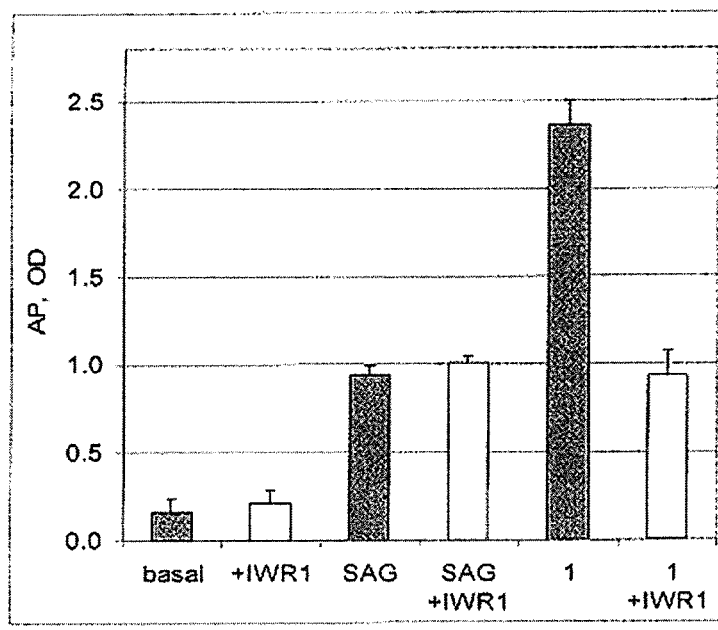
FIG. 7: the IWR1 compound inhibits the activity of compound 1 and does not affect that of SAG. C3H10T1/2 mesenchymal stem cells were treated with compound 1 at 1 µM or SAG at 0.1 µM in the presence (white bars) or absence (gray bars) of 10 µM of IWR1. The alkaline phosphatase enzymatic activity is expressed as OD. A representative experiment with respect to 3 carried out independently. Mean±SEM of quadruplicates.

IWR1 makes it possible to reduce by 60% the activity of compound 1 used at a concentration of 1 µM, whereas it does not modify that of SAG (FIG. 7). A dose-response curve of compound 1 with the IWR1 compound made it possible to deduce an $IC_{50}=2.5$ µM with respect to alkaline phosphatase inhibition. This value is in agreement with the affinity of IWR1 determined by means of a test measuring its inhibition of the Wnt morphogen pathway (induction test using a TCF/luciferase reporter gene) (Chen et al., Nat Chem Biol, 2009).

This experiment indicates that the action of the compounds of general formula (I) involves the axin2 proteins. The role of the axin2 proteins in the control of the activity of β-catenin suggests that the biological activity induced by these compounds could involve the β-catenin pathway. This pathway is associated with multiple pathological conditions, such as colorectal cancers for example. More generally, it is involved in the maintaining of stem cells in tissues in the embryo and the adult, it modulates neurogenesis or is responsible for genetic diseases (see review 2010 by Freese et al.). The identification of selective compounds which make it possible to block the Smo2 binding sites is therefore of great interest.

CONCLUSIONS

These experiments demonstrate that the compounds of general formula (I) can be used in order to identify and select cell differentiation antagonists exhibiting particular structures acting on one or another of the Smo1 or Smo2 sites, or alternatively on both sites. The identification of other biological responses (proliferation, migration, apoptosis, gene induction, etc.) induced by the compounds of the formula (I) will enable the development of tests for identifying compounds which modulate these Smo2 binding sites. These novel compounds will make it possible to modulate these various responses in healthy individuals or individuals suffering from pathological conditions.

REFERENCES

Ahn, S, and A. L. Joyner (2005). "In vivo analysis of quiescent adult neural stem cells responding to Sonic hedgehog." *Nature* 437(7060): 894-7

Angot, E., K. Loulier, et al. (2008). "Chemoattractive activity of sonic hedgehog in the adult subventricular zone modulates the number of neural precursors reaching the olfactory bulb." *Stem Cells* 26(9): 2311-20.

Beachy, P. A., S. S. Karhadkar, et al. (2004). "Tissue repair and stem cell renewal in carcinogenesis." *Nature* 432(7015): 324-31.

Berman, D. M., S. S. Karhadkar, et al. (2002). "Medulloblastoma growth inhibition by hedgehog pathway blockade." *Science* 297(5586): 1559-61.

Brunton, S. A., J. H. Stibbard, et al. (2009). "Potent agonists of the Hedgehog signaling pathway." *Bioorg Med Chem Lett* 19(15): 4308-11.

Charytoniuk, D., E. Traiffort, et al. (2002). "Intrastriatal sonic hedgehog injection increase Patched transcript levels in the adult rat subventricular zone." *Eur J Neurosci* 16(12): 2351-7.

Chen, B., M. E. Dodge, et al. (2009). "Small molecule-mediated disruption of Wnt-dependent signaling in tissue regeneration and cancer." *Nat Chem Biol* 5(2): 100-7.

Chen, J. K., J. Taipale, et al. (2002). "Small molecule modulation of Smoothened activity." *Proc Natl Acad Sci USA* 99(22): 14071-6.

Corcoran, R. B. and M. P. Scott (2006). "Oxysterols stimulate Sonic hedgehog signal transduction and proliferation of medulloblastoma cells." *Proc Natl Acad Sci USA* 103(22): 8408-13.

Coulombe, J., E. Traiffort, et al. (2004). "Hedgehog interacting protein in the mature brain: membrane-associated and soluble forms." *Mol Cell Neurosci* 25(2): 323-33.

Frank-Kamenetsky, M., X. M. Zhang, et al. (2002). "Small-molecule modulators of Hedgehog signaling: identification and characterization of Smoothened agonists and antagonists." *J Biol* 1(2): 10.

Freese, J. L., D. Pino, et al. "Wnt signaling in development and disease." *Neurobiol Dis* 38(2): 148-53.

Ho, K. S, and M. P. Scott (2002). "Sonic hedgehog in the nervous system: functions, modifications and mechanisms." *Curr Opin Neurobiol* 12(1): 57-63.

Incardona, J. P., W. Gaffield, et al. (1998). "The teratogenic Veratrum alkaloid cyclopamine inhibits sonic hedgehog signal transduction." *Development* 125(18): 3553-62.

Ingham, P. W. and A. P. McMahon (2001). "Hedgehog signaling in animal development: paradigms and principles." *Genes Dev* 15(23): 3059-87.

Lai, K., B. K. Kaspar, et al. (2003). "Sonic hedgehog regulates adult neural progenitor proliferation in vitro and in vivo." *Nat Neurosci* 6(1): 21-7.

Loulier, K., M. Ruat, et al. (2006). "Increase of proliferating oligodendroglial progenitors in the adult mouse brain upon Sonic hedgehog delivery in the lateral ventricle." *J Neurochem* 98(2): 530-42.

Lum, L. and P. A. Beachy (2004). "The Hedgehog response network: sensors, switches, and routers." *Science* 304(5678): 1755-9.

Ma, G., Y. Xiao, et al. (2008). "Recent progress in the study of Hedgehog signaling." *J Genet Genomics* 35(3): 129-37.

Ma, Y., A. Erkner, et al. (2002). "Hedgehog-mediated patterning of the mammalian embryo requires transporter-like function of dispatched." *Cell* 111(1): 63-75.

Marti, E. and P. Bovolenta (2002). "Sonic hedgehog in CNS development: one signal, multiple outputs." *Trends Neurosci* 25(2): 89-96.

McMahon, A. P., P. W. Ingham, et al. (2003). "Development roles and clinical significance of hedgehog signaling." *Curr Top Dev Biol* 53: 1-114.

Pepinsky, R. B., R. I. Shapiro, et al. (2002). "Long-acting forms of Sonic hedgehog with improved pharmacokinetic and pharmacodynamic properties are efficacious in a nerve injury model." *J Pharm Sci* 91(2): 371-87.

Pepinsky, R. B., C. Zeng, et al. (1998). "Identification of a palmitic acid-modified form of human Sonic hedgehog." *J Biol Chem* 273(22): 14037-45.

Rohatgi, R., L. Milenkovic, et al. (2009). "Hedgehog signal transduction by Smoothened: pharmacologic evidence for a 2-step activation process." *Proc Natl Acad Sci USA* 106 (9): 3196-201.

Rohatgi, R., L. Milenkovic, et al. (2007). "Patched1 regulates hedgehog signaling at the primary cilium." *Science* 317 (5836): 372-6.

Romer, J. T., H. Kimura, et al. (2004). "Suppression of the Shh pathway using a small molecule inhibitor eliminates medulloblastoma in Ptc1(+/-)p53(-/-) mice." *Cancer Cell* 6(3): 229-40.

Rominger, C. M., W. L. Bee, et al. (2009). "Evidence for allosteric interactions of antagonist binding to the Smoothened receptor." *J Pharmacol Exp Ther* 329(3): 995-1005.

Scales, S. J. and F. J. de Sauvage (2009). "Mechanisms of Hedgehog pathway activation in cancer and implications for therapy." *Trends Pharmacol Sci* 30(6): 303-12.

Sinha, S, and J. K. Chen (2006). "Purmorphamine activates the Hedgehog pathway by targeting Smoothened." *Nat Chem Biol* 2(1): 29-30.

Stecca, B. and A. Ruiz i Altaba (2009). "A GLI1-p53 inhibitory loop controls neural stem cell and tumour cell numbers." *Embo J* 28(6): 663-76.

Taipale, J., J. K. Chen, et al. (2000). "Effects of oncogenic mutations in Smoothened and Patched can be reversed by cyclopamine." *Nature* 406(6799): 1005-9.

Taipale, J., M. K. Cooper, et al. (2002). "Patched acts catalytically to suppress the activity of Smoothened." *Nature* 418(6900): 892-7.

Traiffort, E., D. Charytoniuk, et al. (1999). "Discrete localizations of hedgehog signalling components in the developing and adult rat nervous system." *Eur J Neurosci* 11(9): 3199-214.

Traiffort, E., C. Dubourg, et al. (2004). "Functional characterization of sonic hedgehog mutations associated with holoprosencephaly." *J Biol Chem* 279(41): 42889-97.

Traiffort, E., K. L. Moya, et al. (2001). "High expression and anterograde axonal transport of aminoterminal sonic hedgehog in the adult hamster brain." *Eur J Neurosci* 14(5): 839-50.

Tsuboi, K. and C. W. Shults (2002). "Intrastriatal injection of sonic hedgehog reduces behavioral impairment in a rat model of Parkinson's disease." *Exp Neurol* 173(1): 95-104.

Varjosalo, M. and J. Taipale (2008). "Hedgehog: functions and mechanisms." *Genes Dev* 22(18): 2454-72.

Wang, Y., Z. Zhou, et al. (2009). "Selective translocation of intracellular Smoothened to the primary cilium in response to Hedgehog pathway modulation." *Proc Natl Acad Sci USA* 106(8): 2623-8.

Wechsler-Reya, R. and M. P. Scott (2001). "The developmental biology of brain tumors." *Annu Rev Neurosci* 24: 385-428.

Wilson, C. W., M. H. Chen, et al. (2009). "Smoothened adopts multiple active and inactive conformations capable of trafficking to the primary cilium." *PLoS One* 4(4): e5182.

Wu, X., J. Walker, et al. (2004). "Purmorphamine induces osteogenesis by activation of the hedgehog signaling pathway." *Chem Biol* 11(9): 1229-38.

Yang, H., J. Xiang, et al. (2009). "Converse conformational control of Smoothened activity by structurally related small molecules." *J Biol Chem* 284(31): 20876-84.

Zhao, Y., C. Tong, et al. (2007). "Hedgehog regulates Smoothened activity by inducing a conformational switch." *Nature* 450(7167): 252-8.

The invention claimed is:

1. A method of activating the Hedgehog signaling pathway, comprising bringing a Smoothened receptor and at least one compound of general formula (I) below into contact:

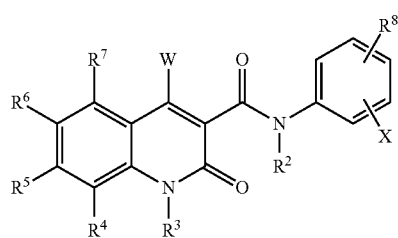

(I)

in which:

X, in the ortho, meta or para position, represents —H, —OH, —NH$_2$, a halogen atom, an alkyl radical consisting of a linear or branched carbon-based chain having from 1 to 10 carbon atoms, an alkoxy radical, a cycloalkyl having from 3 to 8 carbon atoms or an aryl group;

R$^8$, in the ortho, meta or para position, on a carbon other than that which bears the X radical, represents: —(C=O)—NH—R$^1$, —(C=O)—O—R$^1$ or —NH—(C=O)—R$^1$;

W represents —H, —OH, —NH$_2$ or a halogen atom;

R$^1$, R$^2$ and R$^3$, which may be identical or different, and independently of one another, represent:

a hydrogen atom; or an alkyl group consisting of a linear or branched carbon-based chain having from 1 to 10 carbon atoms, optionally unsaturated with one or more double or triple bonds, and optionally substituted with one or more heteroatoms, with one or more halogen atoms or with one or more aryl or heteroaryl groups; or a cycloalkyl having from 3 to 8 carbon atoms, optionally substituted with an alkyl radical consisting of a linear or branched carbon-based chain having from 1 to 10 carbon atoms or an alkoxy radical;

R$^4$, R$^5$, R$^6$ and R$^7$, which may be identical or different, and independently of one another, are chosen from —H, —Cl, —Br, —I, —CN, —NO$_2$, an alkyl radical consisting of a linear or branched carbon-based chain having from 1 to 10 carbon atoms, an alkoxy radical or a cycloalkyl having from 3 to 8 carbon atoms;

wherein R$^3$ and R$^4$ can be fused so as to form, with the adjacent nitrogen and carbon atoms of the quinoline ring which bears them, a 5- or 6-membered ring.

2. The method as claimed in claim 1, wherein the compound of general formula (I) is selected from the group consisting of propyl 4-(1-hexyl-4-hydroxy-2-oxo-1,2-dihydroquinoline-3-carboxamido)benzoate (compound 1);

ethyl 4-(1-benzyl-4-hydroxy-2-oxo-1,2-dihydroquinoline-3-carboxamido)benzoate (compound 2);

ethyl 4-(1-hexyl-4-hydroxy-2-oxo-1,2-dihydroquinoline-3-carboxamido)benzoate (compound 3);

4-(1-hexyl-4-hydroxy-2-oxo-1,2-dihydroquinoline-3-carboxamido)benzoic acid (compound 4);

butyl 4-(1-hexyl-4-hydroxy-2-oxo-1,2-dihydroquinoline-3-carboxamido)benzoate (compound 5);

tert-butyl 4-(1-hexyl-4-hydroxy-2-oxo-1,2-dihydroquinoline-3-carboxamido)benzoate (compound 6);

benzyl 4-(1-hexyl-4-hydroxy-2-oxo-1,2-dihydroquinoline-3-carboxamido)benzoate (compound 7);

N-(4-(butylcarbamoyl)phenyl-1-hexyl-4-hydroxy-2-oxo-1,2-dihydroquinoline-3-carboxamide (compound 8); and isopropyl 4-(1-hexyl-4-hydroxy-2-oxo-1,2-dihydroquinoline-3-carboxamido)benzoate (compound 9).

3. A method for screening for and/or identifying ligands of the Smo2 binding site of the Smoothened receptor, comprising the steps of:

a) bringing the Smoothened receptor and at least one compound of general formula (I) as defined in claim 1 into contact so as to obtain an [Smo-compound of general formula (I)] complex;

b) bringing the Smoothened receptor, said compound of general formula (I) and a test molecule into contact;

c) detecting an interaction between said Smoothened receptor and said test molecules by comparing the Smoothened receptor recovered in step b) with the [Smo-compound of general formula (I)] complex; and d) selecting said test molecules for which an interaction with the Smoothened receptor is measured.

4. The method as claimed in claim 3, wherein step a) is carried out in the liquid phase and in that said step comprises the following steps:
   a) bringing the Smoothened receptor and at least one compound of general formula (I) into contact so as to obtain an [Smo-compound of general formula (I)] complex;
   b) bringing the Smoothened receptor, said compound of general formula (I) and a test molecule into contact;
   c) recovering said Smoothened receptor possibly bound to one or more test molecules and/or to said compound of general formula (I);
   d) detecting an interaction between said Smoothened receptor and said test molecules by comparing the Smoothened receptor recovered in step c) with the [Smo-compound of general formula (I)] complex; and
   e) selecting said test molecules for which an interaction is measured.

5. The method as claimed in claim 3, wherein step a) is carried out on the solid support.

6. The method as claimed in claim 5, wherein the method makes it possible to identify Smoothened receptor ligands which do not bind to the Smo2 binding site.

7. A method for identifying Smoothened receptor agonists, wherein the method comprises the steps of the methods as claimed in claim 3 and the additional steps:
   of bringing said selected molecule into contact with a cell which exhibits a cellular response following activation of the Smoothened receptor and
   of selecting the molecules capable of inducing said cellular response of said cell.

8. A method for identifying a Smoothened receptor antagonist molecule, comprising the following steps:
   a) culturing cells which exhibit a cellular response following the activation of the Smoothened receptor with at least one compound of general formula (I) as defined in claim 1 so as to induce said cellular response;
   b) bringing the cells obtained at the end of step a) into contact with a test molecule;
   c) selecting the molecules which induce an inhibition of said cellular response of said cells.

9. A method for identifying an antagonist molecule molecules capable of inducing a potentiation of Smoothened receptor activation, comprising the following steps:
   a) culturing cells which exhibit a cellular response following the activation of the Smoothened receptor with at least one compound of general formula (I) as defined in claim 1 so as to induce said cellular response;
   b) bringing the cells obtained at the end of step a) into contact with a test molecule;
   c) selecting the molecules which induce an increase in the cellular response of the cells which exhibit a cellular response following the activation of the Smoothened receptor.

10. A kit comprising at least the functional Smoothened receptor and at least one compound of general formula (I) as defined in claim 1.

11. A method for identifying cells, such as tumor cells, expressing the Smoothened receptor, comprising the steps of:
   a) bringing a test cell into contact with a labeled compound of general formula (I) as defined in claim 1;
   b) cleaning the cells in order to remove said labeled compound of general formula (I) which has not bound any receptor of said test cell;
   c) detecting the labeled cells.

* * * * *

UNITED STATES PATENT AND TRADEMARK OFFICE
CERTIFICATE OF CORRECTION

| | | |
|---|---|---|
| PATENT NO. | : 8,957,091 B2 | Page 1 of 1 |
| APPLICATION NO. | : 13/885098 | |
| DATED | : February 17, 2015 | |
| INVENTOR(S) | : Ruat et al. | |

It is certified that error appears in the above-identified patent and that said Letters Patent is hereby corrected as shown below:

In the claims:

Column 28,
Line 25, cancel "such as tumor cells,".

Signed and Sealed this
Fourteenth Day of July, 2015

Michelle K. Lee
*Director of the United States Patent and Trademark Office*